(12) United States Patent
Uhland et al.

(10) Patent No.: US 7,510,551 B2
(45) Date of Patent: Mar. 31, 2009

(54) CONTROLLED RELEASE DEVICE AND METHOD USING ELECTROTHERMAL ABLATION

(75) Inventors: Scott A. Uhland, Roslindale, MA (US); Benjamin F. Polito, Cambridge, MA (US); John M. Maloney, Cambridge, MA (US); Norman F. Sheppard, Jr., Bedford, MA (US); Stephen J. Herman, Andover, MA (US); Barry Y. Yomtov, Marblehead, MA (US)

(73) Assignee: MicroCHIPS, Inc., Bedford, MA (US)

( * ) Notice: Subject to any disclaimer, the term of this patent is extended or adjusted under 35 U.S.C. 154(b) by 556 days.

(21) Appl. No.: 10/641,507

(22) Filed: Aug. 15, 2003

(65) Prior Publication Data

US 2004/0121486 A1  Jun. 24, 2004

Related U.S. Application Data

(60) Provisional application No. 60/463,865, filed on Apr. 18, 2003, provisional application No. 60/404,196, filed on Aug. 16, 2002.

(51) Int. Cl.
*A61K 9/22* (2006.01)
(52) U.S. Cl. .................................................. 604/890.1
(58) Field of Classification Search .............. 604/890.1, 604/891.1, 892.1, 20–21, 65–67, 82–92, 604/244, 246, 256, 285–288, 69, 93.01, 288.01–288.04; 436/174–175
See application file for complete search history.

(56) References Cited

U.S. PATENT DOCUMENTS 3,692,027 A  9/1972  Ellinwood, Jr.
3,952,741 A  4/1976  Baker (Continued)

FOREIGN PATENT DOCUMENTS

DE     197 16 683 C1    6/1998

(Continued)

OTHER PUBLICATIONS

Armani, et al., "Microfabrication Technology for Polycaprolactone, a Biodegradable Polymer," *J. Micromech. Microeng.* 10:80-84 (2000).

(Continued)

*Primary Examiner*—Nicholas D Lucchesi
*Assistant Examiner*—Theodore J Stigell
(74) *Attorney, Agent, or Firm*—Sutherland Asbill & Brennan LLP

(57) ABSTRACT

Devices and methods are provided for the controlled release or exposure of reservoir contents. The device includes a reservoir cap formed of an electrically conductive material, which prevents the reservoir contents from passing out from the device and prevents exposure of the reservoir contents to molecules outside of the device; an electrical input lead connected to said reservoir cap; and an electrical output lead connected to said reservoir cap, such that upon application of an electrical current through the reservoir cap, via the input lead and output lead, the reservoir cap ruptures to release or expose the reservoir contents. The reservoir contents can comprise a release system containing drug molecules for release or can comprise a secondary device, such as a sensor. In one embodiment, the controlled release system is incorporated into an implantable drug delivery device.

50 Claims, 7 Drawing Sheets

U.S. PATENT DOCUMENTS

| | | | |
|---|---|---|---|
| 3,976,983 A | 8/1976 | Moussie | |
| 4,003,379 A | 1/1977 | Ellinwood, Jr. | |
| 4,089,734 A | 5/1978 | Bierig | |
| 4,146,029 A | 3/1979 | Ellinwood, Jr. | |
| 4,209,894 A | 7/1980 | Keen | |
| 4,345,981 A | 8/1982 | Bennett et al. | |
| 4,360,019 A | 11/1982 | Portner et al. | |
| 4,585,652 A | 4/1986 | Miller et al. | |
| 4,793,825 A | 12/1988 | Benjamin et al. | |
| 5,041,107 A | 8/1991 | Heil, Jr. | |
| 5,167,625 A | 12/1992 | Jacobsen et al. | |
| 5,200,051 A | 4/1993 | Cozzette et al. | |
| 5,252,294 A | 10/1993 | Kroy et al. | |
| 5,254,081 A | 10/1993 | Maurer et al. | |
| 5,304,293 A | 4/1994 | Tierney et al. | |
| 5,336,213 A | 8/1994 | D'Angelo et al. | |
| 5,366,454 A | 11/1994 | Currie et al. | |
| 5,368,588 A | 11/1994 | Bettinger | |
| 5,368,704 A | 11/1994 | Madou et al. | |
| 5,380,272 A | 1/1995 | Gross | |
| 5,443,508 A | 8/1995 | Giampapa | |
| 5,493,177 A | 2/1996 | Muller et al. | |
| 5,504,026 A | 4/1996 | Kung | |
| 5,533,995 A | 7/1996 | Corish et al. | |
| 5,605,662 A | 2/1997 | Heller et al. | |
| 5,660,680 A | 8/1997 | Keller | |
| 5,662,689 A | 9/1997 | Elsberry et al. | |
| 5,770,076 A | 6/1998 | Chu et al. | |
| 5,797,898 A * | 8/1998 | Santini et al. | 604/890.1 |
| 5,824,204 A | 10/1998 | Jerman | |
| 5,842,787 A | 12/1998 | Kopf-Sill et al. | |
| 5,843,767 A | 12/1998 | Beattie | |
| 5,863,708 A | 1/1999 | Zanzucchi et al. | |
| 5,949,187 A | 9/1999 | Xu et al. | |
| 5,962,081 A | 10/1999 | Ohman et al. | |
| 5,971,931 A | 10/1999 | Raff | |
| 5,985,328 A | 11/1999 | Chu et al. | |
| 5,989,445 A | 11/1999 | Wise et al. | |
| 6,001,090 A | 12/1999 | Lenhart | |
| 6,027,695 A | 2/2000 | Oldenburg et al. | |
| 6,051,017 A | 4/2000 | Loeb et al. | |
| 6,062,461 A | 5/2000 | Sparks et al. | |
| 6,068,752 A | 5/2000 | Dubrow et al. | |
| 6,081,736 A | 6/2000 | Colvin et al. | |
| 6,114,658 A | 9/2000 | Roth et al. | |
| 6,123,861 A | 9/2000 | Santini, Jr. et al. | |
| 6,129,685 A | 10/2000 | Howard, III | |
| 6,136,212 A | 10/2000 | Mastrangelo et al. | |
| 6,140,740 A | 10/2000 | Porat et al. | |
| 6,161,047 A | 12/2000 | King et al. | |
| 6,171,850 B1 | 1/2001 | Nagle et al. | |
| 6,178,349 B1 | 1/2001 | Kieval | |
| 6,185,455 B1 | 2/2001 | Loeb et al. | |
| 6,214,032 B1 | 4/2001 | Loeb et al. | |
| 6,289,237 B1 | 9/2001 | Mickle et al. | |
| 6,319,241 B1 | 11/2001 | King et al. | |
| 6,334,859 B1 | 1/2002 | Richter | |
| 6,349,232 B1 * | 2/2002 | Gordon | 604/20 |
| 6,378,292 B1 | 4/2002 | Youngner | |
| 6,384,353 B1 | 5/2002 | Huang et al. | |
| 6,403,403 B1 | 6/2002 | Mayer et al. | |
| 6,436,853 B2 | 8/2002 | Lin et al. | |
| 6,437,640 B1 | 8/2002 | Mayer et al. | |
| 6,480,730 B2 | 11/2002 | Darrow et al. | |
| 6,483,368 B2 | 11/2002 | Mayer et al. | |
| 6,491,666 B1 | 12/2002 | Santini, Jr. et al. | |
| 6,527,762 B1 * | 3/2003 | Santini et al. | 604/890.1 |
| 6,537,250 B1 | 3/2003 | Kriesel | |
| 6,537,256 B2 | 3/2003 | Santini, Jr. et al. | |
| 6,551,838 B2 * | 4/2003 | Santini et al. | 436/174 |
| 6,571,125 B2 | 5/2003 | Thompson | |
| 6,587,719 B1 | 7/2003 | Barrett et al. | |
| 6,656,162 B2 | 12/2003 | Santini, Jr. et al. | |
| 6,663,615 B1 | 12/2003 | Madou et al. | |
| 6,669,683 B2 | 12/2003 | Santini, Jr. et al. | |
| 6,733,485 B1 | 5/2004 | Whitehurst et al. | |
| 6,757,560 B1 | 6/2004 | Fischer et al. | |
| 6,908,770 B1 | 6/2005 | McDevitt et al. | |
| 6,968,743 B2 | 11/2005 | Rich et al. | |
| 7,010,345 B2 | 3/2006 | Hill et al. | |
| 2001/0053885 A1 | 12/2001 | Gielen et al. | |
| 2002/0022826 A1 | 2/2002 | Reynolds et al. | |
| 2002/0038137 A1 | 3/2002 | Stein | |
| 2002/0055761 A1 | 5/2002 | Mann et al. | |
| 2002/0072734 A1 | 6/2002 | Liedtke | |
| 2002/0072784 A1 | 6/2002 | Sheppard, Jr. et al. | |
| 2002/0082665 A1 | 6/2002 | Haller et al. | |
| 2002/0099359 A1 | 7/2002 | Santini, Jr. et al. | |
| 2002/0107470 A1 | 8/2002 | Richards et al. | |
| 2002/0107553 A1 | 8/2002 | Hill et al. | |
| 2002/0111601 A1 | 8/2002 | Thompson | |
| 2002/0119176 A1 * | 8/2002 | Greenberg et al. | 424/422 |
| 2002/0138067 A1 | 9/2002 | Sheppard, Jr. et al. | |
| 2002/0143369 A1 | 10/2002 | Hill et al. | |
| 2002/0144548 A1 | 10/2002 | Cohn et al. | |
| 2002/0151776 A1 | 10/2002 | Shawgo et al. | |
| 2002/0165586 A1 | 11/2002 | Hill et al. | |
| 2002/0183721 A1 | 12/2002 | Santini, Jr. et al. | |
| 2002/0187260 A1 | 12/2002 | Sheppard, Jr. et al. | |
| 2002/0188282 A1 | 12/2002 | Greenberg | |
| 2003/0004549 A1 | 1/2003 | Hill et al. | |
| 2003/0010808 A1 | 1/2003 | Uhland et al. | |
| 2003/0032946 A1 | 2/2003 | Fishman | |
| 2003/0036794 A1 | 2/2003 | Ragheb et al. | |
| 2003/0069560 A1 | 4/2003 | Adamis et al. | |
| 2003/0104590 A1 | 6/2003 | Santini, Jr. et al. | |
| 2003/0105455 A1 | 6/2003 | Santini, Jr. et al. | |
| 2005/0100937 A1 | 5/2005 | Holmes | |

FOREIGN PATENT DOCUMENTS

| | | |
|---|---|---|
| WO | WO 02/056862 A2 | 7/2002 |
| WO | WO 02/058678 A2 | 8/2002 |

OTHER PUBLICATIONS

Bhattacharya, et al., "Next Generation Integral Passives: Materials, Processes, and Integration of Resistors and Capacitors on PWB Substrates," *J. Mat. Sci. Mat. Electronics* 11:253-68 (2000).

Bae, et al., "Pulsatile Drug Release by Electric Stimulus," ACS Symp. Series *Polymeric Drugs & Drug Admin.*, pp. 99-110 (1994).

Cheng, et al., "Localized Silicon Fusion and Eutectic Bonding for MEMS Fabrication and Packaging," *J. Microelectromechanical Syst.* 9:3-8 (2000).

Ehrick, et al., "Artificial Muscle-Based Microactuators for Reversible Controlled Release," ACS Abstracts, No. 22, 222nd ACS Nat'l Meeting (Chicago, 2001) (abstract).

Haroun, et al., "Local Drug Delivery," *Curr. Opin. Oncol.* 12(3): 187-93 (2000) (abstract).

Jackman, et al., "Fabricating Large Arrays of Microwells with Arbitrary Dimensions and Filling them Using Discontinuous Dewetting," *Anal. Chem.* 70:2280-87 (1998).

Liu, et al., "Applications of Microfabrication and Micromachining Techniques to Biotechnology," *Tibtech* 15:213-16 (1997).

Low, et al., "Microactuators Toward Microvalves for Responsive Controlled Drug Delivery," *Sensors & Actuators* B 67: 149-60 (2000).

Madou, et al., "Exploitation of a Novel Artificial Muscle for Controlled Drug Delivery," *Polym. Mater. Sci. Eng.* 83: 495-497 (2000).

Madou, "Fundamentals of Microfabrication," pp. 468-514 (CRC Press 1997).

Santini, et al., "Microchips as Controlled Drug-Delivery Devices," *Angew Chem. Int. Ed. Engl.* 39(14): 2396-407 (2000).

Santini, et al., "Microchip Technology in Drug Delivery," *Ann. Med.* 32(6) 377-79 (2001).

Santini, et al., "A Controlled-Release Microchip," *Nature* 397(6717): 335-38 (1999).

Surbled, et al., "Array of Shape Memory Alloy One-Shot Micro-Valves for Drug Delivery," MME '99, Gif sur Yvette, France (Sep. 27-28, 1999).

Surbled, et al., "Characterization of Sputtered TiNi Shape Memory Alloy Thin Films," *Jpn. J. Applied Phys.* 38: L 1547-49 (1999).

Surbled, et al., "Shape Memory Alloys for Micromembranes Actuation," *SPIE* 3825: 63-70 (1999).

Tao, et al., "Microfabricated Drug Delivery Systems: From Particles to Pores," *Adv. Drug Deliv. Res.* 55(3): 315-28 (2003).

Tierney, et al., "Electroreleasing Composite Membranes for Delivery of Insulin and Other Biomacromolecules," *J. Electrochem Soc.* 137(6): 2005-06 (1990).

Tierney, et al., "New Electrorelease Systems Based on Microporous Membranes," *J. Electrochem Soc.* 137(12): 3789-93 (1990).

Vladimirsky, et al., "Thin Metal Film Thermal Micro-Sensors," Proc. SPIE 2640: 184-92 (1995).

Wogiersien, et al., "Fabrication of Thin Film Resistors and Silicon Microstructures Using a Frequency-Doubled Nd:YAG Laser," *Proc. SPIE—Design, Test, and Microfabrication of MEMS and MOEMS*, 2: 1105 (Paris, Mar. 1999).

Yao, et al., "Low Temperature Eutectic Bonding for In-Plane Type Micro Thermoelectric Cooler," *Proc. ASME Intl. Mech. Eng. Congr. & Expo* 2001.

Office Action mailed May 5, 2008 in U.S. Appl. No. 10/654,761.
Amendment and Response to Office Action filed Mar. 31, 2008 in U.S. Appl. No. 10/654,761.
Office Action mailed Oct. 29, 2007 in U.S. Appl. No. 10/654,761.
Amendment and Response to Office Action filed Sep. 24, 2007 in U.S. Appl. No. 10/654,761.
Office Action mailed Apr. 27, 2007 in U.S. Appl. No. 10/654,761.
Amendment and Response to Office Action filed Apr. 4, 2008 in U.S. Appl. No. 10/679,763.
Office Action mailed Oct. 10, 2007 in U.S. Appl. No. 10/679,763.
Response to Office Action filed Sep. 26, 2007 in U.S. Appl. No. 10/679,763.
Response to Office Action filed Mar. 19, 2007 in U.S. Appl. No. 10/679,763.
Office Action mailed Dec. 19, 2006 in U.S. Appl. No. 10/679,763.
Office Action mailed Apr. 16, 2008 in U.S. Appl. No. 10/679,772.
Amendment and Response to Office Action filed Aug. 28, 2007 in U.S. Appl. No. 10/679,772.
Office Action mailed Apr. 10, 2007 in U.S. Appl. No. 10/679,772.
Amendment and Response to Office Action filed Nov. 8, 2006 in U.S. Appl. No. 10/679,772.
Amendment and Response to Office Action filed Sep. 21, 2006 in U.S. Appl. No. 10/679,772.
Office Action mailed Jun. 23, 2006 in U.S. Appl. No. 10/679,772.

* cited by examiner

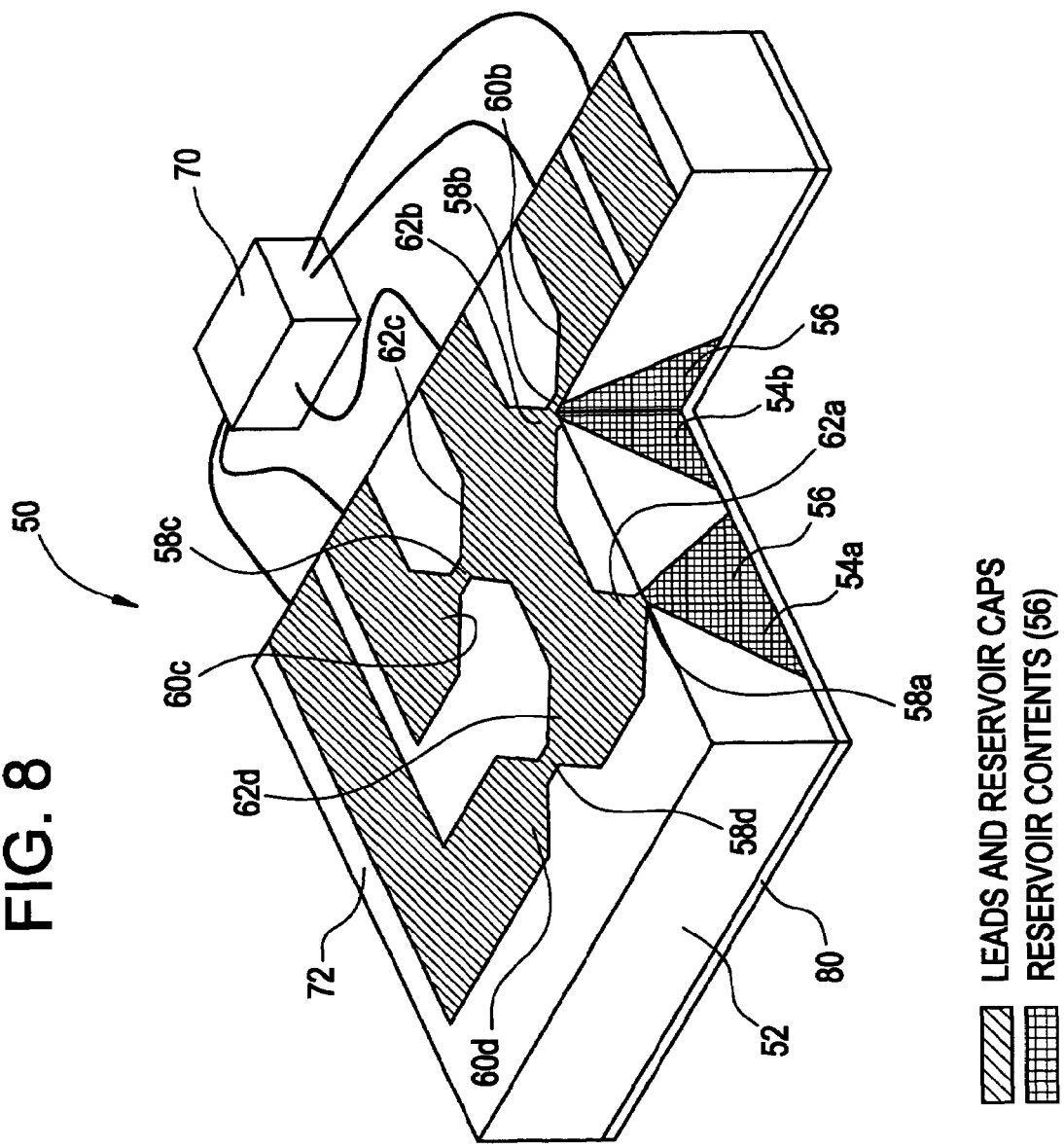

CONTROLLED RELEASE DEVICE AND METHOD USING ELECTROTHERMAL ABLATION

CROSS-REFERENCE TO RELATED APPLICATIONS

Priority is claimed to U.S. provisional application Serial No. 60/404,196, filed Aug. 16, 2002, and U.S. provisional application Serial No. 60/463,865, filed Apr. 18, 2003.

BACKGROUND OF THE INVENTION

This invention relates to devices and methods for the controlled exposure or release of molecules (such as drugs), microsized secondary devices (such as sensors), or combinations thereof.

U.S. Pat. No. 5,797,898, No. 6,551,838, and No. 6,527,762, all to Santini Jr., et al., disclose microchip delivery devices which have a plurality, typically hundreds to thousands, of reservoirs in which each reservoir has a reservoir cap positioned on the reservoir over the reservoir contents. For example, the contents, which can be a quantity of chemical molecules (e.g., drugs) or smaller devices, in each reservoir are selectively released or exposed by the controlled removal of the reservoir cap. The reservoir opening mechanism may, for example, be disintegration by electrochemical oxidation or mechanical rupture.

It would be desirable to provide new and improved technology for the controlled opening, i.e., activation, of microreservoirs in microchip or other devices. For example, the activation technology preferably would operate effectively independent of its location or environment for operation. In addition, the activation technology desirably would be robust, for example, such that surface contamination of the device (e.g., at the reservoir caps) minimally, if at all, affects its release performance. A sufficiently robust or energetic activation method could also be compatible with applied coatings that might otherwise impede activation. Such coatings could be added to enhance device strength, biocompatibility, biostability, and/or hermeticity.

Furthermore, it would be advantageous to have to a convenient means for determining that a particular reservoir of a microchip device has been activated as directed. That is, that the reservoir intended to have been opened is in fact open. Such verification techniques would be highly beneficial to demonstrate release of drug molecules or other contents from the reservoirs, ensuring reliable and consistent operation. It would be further desirable, particularly if active devices have many reservoirs, to provide a simplified means for electrically addressing each of the reservoirs.

SUMMARY OF THE INVENTION

Devices and methods are provided for the controlled release or exposure of reservoir contents. In one aspect, the device includes a reservoir cap formed of an electrically conductive material, which prevents the reservoir contents from passing out from the device and prevents exposure of the reservoir contents to molecules outside of the device; an electrical input lead connected to said reservoir cap; and an electrical output lead connected to said reservoir cap, such that upon passage of an electrical current through the reservoir cap, via the input lead and output lead, the reservoir cap is locally heated to rupture the reservoir cap to release or expose the reservoir contents.

The reservoir cap and leads include an electrically conductive material. The electrically conductive material can be a single component or multi-component metal or semiconductor. Representative examples of suitable materials include gold, platinum, titanium, platinum-iridium, nickel-titanium, gold-silicon, and silicon doped with an impurity to increase electrical conductivity. In one embodiment, the reservoir cap is in the form of a thin metal or semiconductor film. In another embodiment, the reservoir cap is in the form of multiple layers of different metals, semiconductors, or combinations thereof.

In one embodiment, the reservoir cap and conductive leads are formed of the same material, and the temperature of the reservoir cap increases locally under applied current because the reservoir cap is suspended in a medium that is less thermally conductive than the substrate. Alternatively, the reservoir cap and conductive leads are formed of the same material, and the reservoir cap has a smaller cross-sectional area in the direction of electric current flow. The increase in current density through the reservoir cap causes an increase in localized heating. One technique for increasing the current density is to fabricate leads and reservoir caps that have the same thickness, while the ratio of the width of the leads to the width of the reservoir cap is increased, preferably to 2:1 or more. Increased current density also can be achieved by fabricating reservoir caps with a thickness that is less than the thickness of the leads. In other embodiments, the reservoir cap is formed of a material that is different from the material forming the leads, wherein the material forming the reservoir cap has a different electrical resistivity, thermal diffusivity, thermal conductivity, and/or a lower melting temperature than the material forming the leads. Various combinations of these embodiments can be employed.

In another aspect, a device is provided for the controlled release or exposure of reservoir contents comprising: a substrate; a plurality of reservoirs in the substrate; reservoir contents comprising molecules, a secondary device, or both, located in the plurality of reservoirs; a reservoir cap covering each reservoir to isolate the reservoir contents within the reservoir, each reservoir cap comprising an electrically conductive material; a pair of conductive leads electrically connected to said reservoir cap, the pair comprising an electrical input lead and an electrical output lead; and a source of electric power for applying an electrical current through each reservoir cap, via said pair of conductive leads, in an amount effective to locally heat the reservoir cap to cause the reservoir cap to rupture and thus open the reservoir.

In another aspect, the device includes an electrical component or system for detecting an open electrical circuit between the leads of a reservoir cap that has been ruptured, to verify reservoir opening.

In one embodiment, the device comprises at least four reservoirs or more positioned in a two-dimensional array in the substrate, for example, wherein the input leads of the reservoir caps are electrically connected in parallel by rows of the array and the output leads of the reservoir caps are electrically connected in parallel by columns of the array. This embodiment also provides simplified input/output (I/O) requirement.

In one embodiment, the reservoir contents comprise a release system containing drug molecules for release. In another embodiment, the reservoir contents comprise secondary devices, such as sensors or sensor components.

Optionally, the reservoir cap, the leads, or both can further comprise a protective or structurally supporting layer of a dielectric material, such as silicon dioxide, in addition to the electrically conductive material.

In various embodiments, the device can be a subcomponent of an implantable drug delivery device. Such a device may further comprise a sensor indicative of a physiological condition, an electrode for providing electrical stimulation to the body, a catheter, a pump, or a combination thereof. In one embodiment, the device is part of a microchip device.

In another aspect, methods are provided for the controlled delivery of molecules. In one embodiment, the steps include positioning at a preselected location a device which provides the controlled release of molecules, the device having the molecules for delivery and a reservoir cap formed of an electrically conductive material which prevents said molecules for delivery from passing out from the device; and applying an electrical current through said reservoir cap, via an electrical input lead and an electrical output lead which are electrically connected to said reservoir cap, to locally heat the reservoir cap to cause the reservoir cap to rupture to enable the molecules to pass outward from the device to the preselected location. In one embodiment, the site is internal to a patient in need of the molecules being released.

In another aspect, methods are provided for the controlled exposure of reservoir contents. In one embodiment, the steps include positioning at a preselected location a device which provides controlled exposure of reservoir contents, the device having reservoir contents and a reservoir cap formed of an electrically conductive material which prevents exposure of the reservoir contents to molecules outside of the device at the preselected location; and applying an electrical current through said reservoir cap, via an electrical input lead and an electrical output lead which are electrically connected to said reservoir cap, to locally heat the reservoir cap to cause the reservoir cap to rupture to expose the reservoir contents to said molecules at the preselected location. In one embodiment, the site is internal to a patient and the reservoir contents comprise a sensor or sensor component for sensing a physiological condition.

In another aspect, methods are provided for fabricating a device for the controlled exposure or release of molecules or secondary devices. In one embodiment, the method steps include (i) forming a plurality of reservoirs in a substrate; (ii) capping each of said reservoirs with an electrically conductive reservoir cap; (iii) loading the reservoirs with reservoir contents; (iv) forming in operable connection with each reservoir cap an electrical input lead and an electrical output lead; and (v) providing an electrical current supply and distribution means capable of selectively passing an electrical current through each reservoir cap, via the input lead and output lead, in an amount effective to locally heat the reservoir cap to cause the reservoir cap to rupture and thus open the reservoir.

BRIEF DESCRIPTION OF THE DRAWINGS

FIG. 8 is a perspective/cross-sectional view of a portion of one embodiment of a device having an array of four reservoirs, a reservoir cap covering each reservoir to isolate the reservoir contents within each reservoir, a pair of conductive leads electrically connected to said reservoir cap, and a source of electric power for applying an electrical current through each reservoir cap.

DETAILED DESCRIPTION OF THE INVENTION

Figure 1A:
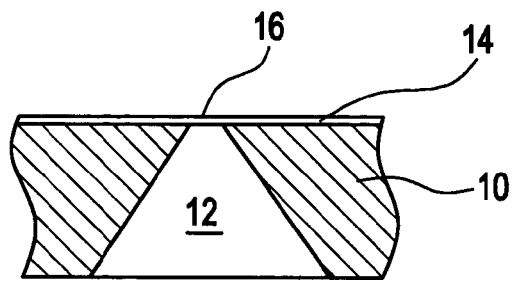
FIGS. 1A-B illustrate a cross-sectional view (FIG. 1A) and a plan view (FIG. 1B) of one embodiment of a portion of a device in which the reservoir cap and leads are formed of the same material.

Electrothermal ablation reservoir opening devices, systems, and methods have been developed, for controlled reservoir opening. Generally, the device has a reservoir cap that is positioned over a reservoir opening to block the opening until release or exposure of the reservoir contents is desired and that functions as a heat generator. Electric current is used to provide local heating of the reservoir cap in an amount effective to rupture the reservoir cap, opening the reservoir. As used herein, the term "rupture" refers to an electrically-induced thermal shock that causes the reservoir cap structure to fracture, and/or to a loss of structural integrity of the reservoir cap due to a phase change, (e.g., melting or vaporization), either or both of which are caused by the generation of heat within the reservoir cap as a result of electric current flowing through the reservoir cap. While not being bound to any theory, the heating causes the reservoir cap to degrade by melting (or vaporizing), thermal shock, and/or a mismatch in the coefficient of thermal expansion, thereby displacing the reservoir cap from over the reservoir and/or creating an aperture through the reservoir cap. This activation mechanism does not depend on a separate resistive heater element, for example, attached to an outer surface of a reservoir. (This rupture process is analogous to the process by which a conventional simple electrical fuse heats and then disintegrates (e.g., burns up) upon passage of an excessive amount of electrical current through it.)

As used herein, the term "local heating" in reference to the reservoir cap refers to a significant temperature rise, which is local to the reservoir cap (e.g., the midpoint of the reservoir cap could be the hottest point). This temperature rise results from two phenomena: the heat generation and the heat loss occurring in the device. In preferred embodiments, the local heating and rupturing occurs very quickly, on the order of 10 to 50 µs, which allows little heat to pass into the surrounding environment or into the reservoir contents, thereby minimizing any temperature increase in the environment surrounding the reservoir or limiting any temperature increase to the region immediately surrounding the reservoir cap.

As used herein, the terms "comprise," "comprising," "include," and "including" are intended to be open, non-limiting terms, unless the contrary is expressly indicated.

Opening System Components and Devices

The opening, or activation, systems and devices described herein can be used with or incorporated into a variety of devices, including implantable drug delivery devices, such as the microchip devices described in U.S. Pat. No. 5,797,898, No. 6,551,838, No. 6,527,762, as well as in U.S. patent application publications No. 2002/0099359 and No. 2003/0010808, which are incorporated herein by reference. In some embodiments, the activation release device and system is a subcomponent of another device. For example, it may be part of an implantable drug delivery device that further comprises a sensor indicative of a physiological condition of a patient, an electrode for providing electrical stimulation to the body of a patient, a pump, a catheter, or a combination thereof.

Substrate and Reservoirs

The substrate is the structural body (e.g., part of a device) in which the reservoirs are formed, e.g., it contains the etched, machined, or molded reservoirs. A reservoir is a well, a container. MEMS methods, micromolding, and micromachining techniques known in the art can be used to fabricate the substrate/reservoirs from a variety of materials. See, for example, U.S. Pat. No. 6,123,861 and U.S. Patent Application Publication No. 2002/0107470. Examples of suitable substrate materials include metals, ceramics, semiconductors, and degradable and non-degradable polymers. Biocompatibility of the substrate material typically is preferred for in vivo device applications. The substrate, or portions thereof, may be coated, encapsulated, or otherwise contained in a biocompatible material (e.g., poly(ethylene glycol), polytetrafluoroethylene-like materials, inert ceramics, titanium, and the like) before use.

The substrate can be flexible or rigid. In one embodiment, the substrate serves as the support for a microchip device. In one example, the substrate is formed of silicon.

The substrate can have a variety of shapes, or shaped surfaces. It can, for example, have a release side (i.e., an area having reservoir caps) that is planar or curved. The substrate may, for example, be in a shape selected from disks, cylinders, or spheres. See, e.g., FIGS. 9, 11., which are described below. In one embodiment, the release side can be shaped to conform to a curved tissue surface. This would be particularly advantageous for local delivery of a therapeutic agent to that tissue surface. In another embodiment, the back side (distal the release side) is shaped to conform to an attachment surface.

The substrate may consist of only one material, or may be a composite or multi-laminate material, that is, composed of several layers of the same or different substrate materials that are bonded together.

In one embodiment, the substrate is impermeable (at least during the time of use of the reservoir device) to the molecules to be delivered and to surrounding gases or fluids (e.g., water, blood, electrolytes or other solutions).

In another embodiment, the substrate is made of a strong material that degrades or dissolves over a defined period of time into biocompatible components. Examples of biocompatible polymers include poly(lactic acid)s, poly(glycolic acid)s, and poly(lactic-co-glycolic acid)s, as well as degradable poly(anhydride-co-imides).

The substrate thickness can vary depending upon the particular device and application using the activation system described herein. For example, the thickness of a device may vary from approximately 10 µm to several centimeters (e.g., 500 µm). Total substrate thickness and reservoir volume can be increased by bonding or attaching wafers or layers of substrate materials together. The device thickness may affect the volume of each reservoir and/or may affect the maximum number of reservoirs that can be incorporated onto a substrate. The size and number of substrates and reservoirs can be selected to accommodate the quantity and volume of reservoir contents needed for a particular application, although other constraints such as manufacturing limitations or total device size limitations (e.g., for implantation into a patient) also may come into play. For example, devices for in vivo applications desirably would be small enough to be implanted using minimally invasive procedures. Devices for in vitro applications typically have fewer size restrictions.

The substrate can have one, two, or preferably many, reservoirs. In various embodiments, tens, hundreds, or thousands of reservoirs are arrayed across the substrate. For instance, one embodiment of an implantable drug delivery device includes between 250 and 750 reservoirs, where each reservoir contains a single dose of a drug for release, which for example could be released daily over a period of several months to two years. More or less frequent dosing schedules and shorter or longer treatment durations are of course possible.

In one embodiment, the reservoir has a volume equal to or less than 500 µL (e.g., less than 250 µL, less than 100 µL, less than 50 µL, less than 25 µL, less than 10 µL, etc.) and greater than about 1 nL (e.g., greater than 5 nL, greater than 10 nL, greater than about 25 nL, greater than about 50 nL, greater than about 1 µL, etc.).

Reservoir Contents

The reservoir contents is essentially any object or material that needs to be isolated (e.g., protected from) the environment outside of the reservoir until a selected point in time, when its release or exposure is desired. In various embodiments, the reservoir contents comprise (a quantity of) molecules, a secondary device, or a combination thereof. Proper functioning of certain reservoir contents, such as a catalyst or sensor, generally does not require release from the reservoir; rather their intended function, e.g., catalysis or sensing, occurs upon exposure of the reservoir contents to the environment outside of the reservoir after opening of the reservoir cap. Thus, the catalyst molecules or sensing component can be released or can remain immobilized within the open reservoir. Other reservoir contents such as drug molecules often may need to be released from the reservoir in order to pass from the device and be delivered to a site in vivo to exert a therapeutic effect on a patient. However, the drug molecules may be retained for certain in vitro applications.

Molecules

The reservoir contents can include essentially any natural or synthetic, organic or inorganic molecule or mixture thereof. The molecules may be in essentially any form, such as a pure solid or liquid, a gel or hydrogel, a solution, an emulsion, a slurry, or a suspension. The molecules of interest may be mixed with other materials to control or enhance the rate and/or time of release from an opened reservoir. In various embodiments, the molecules may be in the form of solid mixtures, including amorphous and crystalline mixed powders, monolithic solid mixtures, lyophilized powders, and solid interpenetrating networks. In other embodiments, the molecules are in liquid-comprising forms, such as solutions, emulsions, colloidal suspensions, slurries, or gel mixtures such as hydrogels.

For in vivo applications, the chemical molecule can be a therapeutic, prophylactic, or diagnostic agent. As used herein, the term "drug" includes any therapeutic or prophylactic agent (e.g., an active ingredient). The drug can comprise small molecules, large (i.e., macro-) molecules, or a combination thereof, having a bioactive effect. In one embodiment, the large molecule drug is a protein or a peptide. In various embodiments, the drug can be selected from amino acids, nucleic acids, oligonucleotides, polysaccharides, and synthetic organic molecules. In one embodiment, the drug is selected from nucleosides, nucleotides, and analogs and conjugates thereof. Representative examples of drugs include analgesics, anesthetics, anti-angiogenic molecules, antibiotics, antibodies, antineoplastic agents, antioxidants, antiviral agents, chemotherapeutic agents, gene delivery vectors, immunomodulators, ion channel regulators, metabolites, sugars, psychotropic agents, vaccines, vitamins. An example of a diagnostic agent is an imaging agent such as a contrast agent.

In one embodiment, the drug is a protein drug. Examples of suitable types of proteins include glycoproteins, enzymes (e.g., proteolytic enzymes), hormones (e.g., LHRH, steroids, corticosteroids), antibodies, cytokines (e.g., $\alpha$-, $\beta$-, or $\gamma$-interferons), interleukins (e.g., IL-2), and insulin. In one exemplary embodiment, the drug is a bisphosphonate. In another exemplary embodiment, the drug is parathyroid hormone, such as a human parathyroid hormone, e.g., hPTH(1-84) or hPTH(1-34). In a still further embodiment, the drug is a peptide with natriuretic activity, such as BNP. In yet another embodiment, the drug is a calcitonin. In a further embodiment, the drug is selected from diuretics, vasodilators, inotropic agents, anti-arrhythmic agents, $Ca^+$ channel blocking agents, anti-adrenergics/sympatholytics, and renin angiotensin system antagonists.

In one embodiment, the drug is a VEGF inhibitor, VEGF antibody, VEGF antibody fragment, or another anti-angiogenic agent. Examples include an aptamer, such as MACUGEN™ (Pfizer/Eyetech) (pegaptanib sodium)) or LUCENTIS™ (Genetech/Novartis) (rhuFab VEGF, or ranibizumab). These could be used in the prevention of choroidal neovascularization, which would be useful in the treatment of age-related macular degeneration or diabetic retinopathy.

In various embodiments, the drug molecules for release can be PEGylated, a technique known in the art to extend the in vivo lifetime of a bioactive molecule, for example by attaching the bioactive molecule to PEG or another oligomeric or polymeric stabilizing agent. For example, MACUGEN™ is an oligonucleotide with a molecular weight of ~50 KD, about 40 KD of which is an attached PEG molecule. The controlled release devices described herein can deliver such molecules. Advantageously, however, the controlled release devices described herein may obviate the need to PEGylate the bioactive molecule, since the bioactive molecule can be released as and when needed. That is, the devices can deliver an accurate and effective amount of drug at the desired time, avoiding the need to modify the drug (which can be costly and/or difficult to achieve) in order to keep a constant level of the bioactive molecule in the body over an extended period of time.

In one embodiment, the drug is a prostaglandin, a prostacyclin, or another drug effective in the treatment of peripheral vascular disease.

In one embodiment, a device is used to deliver a drug systemically to a patient in need thereof. In another embodiment, the construction and placement of the microchip in a patient enables the local or regional release of drugs that may be too potent for systemic delivery of an effective dose. The reservoir contents in one reservoir or in one device can include a single drug or a combination of two or more drugs, and the reservoir contents can further include pharmaceutically acceptable carriers.

The molecules can be provided as part of a "release system," as taught in U.S. Pat. No. 5,797,898, the degradation, dissolution, or diffusion properties of which can provide a method for controlling the release rate of the molecules. The release system may include one or more pharmaceutical excipients. Suitable pharmaceutically acceptable excipients include most carriers approved for parenteral administration, including various aqueous solutions (e.g., saline, Ringer's, Hank's, and solutions of glucose, lactose, dextrose, ethanol, glycerol, albumin, and the like). Examples of other excipients and diluents include calcium carbonate and sugars. Other excipients may be used to maintain the drug in suspensions as an aid to reservoir filling, stability, or release. Depending on the properties of the drug, such excipients may be aqueous or non-aqueous, hydrophobic or hydrophilic, polar or non-polar, protic or aprotic. Such excipients generally have low reactivity. See.e.g., U.S. Pat. No. 6,264,990 to Knepp et al. The release system optionally includes stabilizers, antioxidants, antimicrobials, preservatives, buffering agents, surfactants, and other additives useful for storing and releasing molecules from the reservoirs in vivo.

The release system may provide a more continuous or consistent release profile (e.g., pulsatile) or constant plasma level as needed to enhance a therapeutic effect, for example. Pulsatile release can be achieved from an individual reservoir, from a plurality of reservoirs, or a combination thereof. For example, where each reservoir provides only a single pulse, multiple pulses (i.e. pulsatile release) are achieved by temporally staggering the single pulse release from each of several reservoirs. Alternatively, multiple pulses can be achieved from a single reservoir by incorporating several layers of a release system and other materials into a single reservoir. Continuous release can be achieved by incorporating a release system that degrades, dissolves, or allows diffusion of molecules through it over an extended period. In addition, continuous release can be approximated by releasing several pulses of molecules in rapid succession ("digital" release, analogous to the digital storage and reproduction of music). The active release systems described herein can be used alone or on combination with passive release systems known in the art, for example, as described in U.S. Pat. No. 5,797,898. For example, the reservoir cap can be removed by electrothermal ablation as described herein to expose a passive release system that only begins its passive release after the reservoir cap has been actively removed. Alternatively, a given substrate can include both passive and active release reservoirs.

For in vitro applications, the molecules can be any of a wide range of molecules where the controlled release of a small (milligram to nanogram) amount of one or more molecules is required, for example, in the fields of analytic chemistry or medical diagnostics. Molecules can be effective as pH buffering agents, diagnostic reagents, and reagents in complex reactions such as the polymerase chain reaction or other nucleic acid amplification procedures. In various other embodiments, the molecules to be released are fragrances or scents, dyes or other coloring agents, sweeteners or other concentrated flavoring agents, or a variety of other compounds. In yet other embodiments, the reservoirs contain immobilized molecules. Examples include any chemical species which can be involved in a reaction, including reagents, catalysts (e.g., enzymes, metals, and zeolites), proteins, nucleic acids, polysaccharides, cells, and polymers, as well as organic or inorganic molecules which can function as a diagnostic agent.

Secondary Devices

As used herein, unless explicitly indicated otherwise, the term "secondary device" includes any device or a component thereof which can be located in a reservoir. In one embodiment, the secondary device is a sensor or sensing component thereof. As used herein, a "sensing component" includes a component utilized in measuring or analyzing the presence, absence, or change in a chemical or ionic species, energy, or one or more physical properties (e.g., pH, pressure) at a site. Types of sensors include biosensors, chemical sensors, physical sensors, or optical sensors. Examples of biosensors that could be adapted for use in/with the reservoir devices described herein include those taught in U.S. Pat. No. 6,486,588; No. 6,475,170; and No. 6,237,398. Secondary devices are further described in U.S. Pat. No. 6,551,838.

Examples of sensing components include components utilized in measuring or analyzing the presence, absence, or change in a drug, chemical, or ionic species, energy (or light), or one or more physical properties (e.g., pH, pressure) at a site. In one embodiment, a device is provided for implantation in a patient (e.g., a human or other mammal) and the reservoir contents comprises at least one sensor indicative of a physiological condition in the patient. For example, the sensor could monitor the concentration of glucose, urea, calcium, or a hormone present in the blood, plasma, interstitial fluid, or other bodily fluid of the patient.

Several options exist for receiving and analyzing data obtained with secondary devices located within the primary device, which can be a microchip device or another device. Devices may be controlled by local microprocessors or remote control. Biosensor information may provide input to the controller to determine the time and type of activation automatically, with human intervention, or a combination thereof. For example, the operation of an implantable drug delivery system (or other controlled release/controlled reservoir exposure system) can be controlled by an on-board microprocessor (i.e., within the package of the implantable device). The output signal from the device, after conditioning by suitable circuitry if needed, will be acquired by the microprocessor. After analysis and processing, the output signal can be stored in a writeable computer memory chip, and/or can be sent (e.g., wirelessly) to a remote location away from the implantable device. Power can be supplied to the implantable device locally by a battery or remotely by wireless transmission. See, e.g., U.S. Patent Application Publication No. 2002/0072784.

In one embodiment, a device is provided having reservoir contents that include drug molecules for release and a sensor/sensing component. For example, the sensor or sensing component can be located in a reservoir or can be attached to the device substrate. The sensor can operably communicate with the device, e.g., through a microprocessor, to control or modify the drug release variables, including dosage amount and frequency, time of release, effective rate of release, selection of drug or drug combination, and the like. The sensor or sensing component detects (or not) the species or property at the site of in vivo implantation and further may relay a signal to the microprocessor used for controlling release from the device. Such a signal could provide feedback on and/or finely control the release of a drug. In another embodiment, the device includes one or more biosensors (which may be sealed in reservoirs until needed for use) that are capable of detecting and/or measuring signals within the body of a patient.

As used herein, the term "biosensor" includes sensing devices that transduce the chemical potential of an analyte of interest into an electrical signal, as well as electrodes that measure electrical signals directly or indirectly (e.g., by converting a mechanical or thermal energy into an electrical signal). For example, the biosensor may measure intrinsic electrical signals (EKG, EEG, or other neural signals), pressure, temperature, pH, or loads on tissue structures at various in vivo locations. The electrical signal from the biosensor can then be measured, for example by a microprocessor/controller, which then can transmit the information to a remote controller, another local controller, or both. For example, the system can be used to relay or record information on the patient's vital signs or the implant environment, such as drug concentration.

Reservoir Caps and Electrical Leads

The reservoir cap is operably (i.e. electrically) connected to an electrical input lead and to an electrical output lead, to facilitate flow of an electrical current through the reservoir cap. When an effective amount of an electrical current is applied through the leads and reservoir cap, the temperature of the reservoir cap is locally increased due to resistive heating, and the heat generated within the reservoir cap increases the temperature sufficiently to cause the reservoir cap to be electrothermally ablated (i.e., ruptured).

As used herein, the term "reservoir cap" refers to a membrane, thin film, or other structure suitable for separating the contents of a reservoir from the environment outside of the reservoir. It generally is self-supporting across the reservoir opening, although support structures (e.g., beams, mesh, and the like) could be built into or onto the reservoir cap. Selectively removing the reservoir cap will then expose the contents of the reservoir to the environment. As used herein, the term "environment" refers to the environment external the reservoirs, including biological fluids and tissues at a site of implantation, air, fluids, and particulates present during storage or in vitro use of a device incorporating the activation system described herein.

The reservoir cap and leads include an electrically conductive material. The reservoir cap can be made from various materials selected to provide a known electrical resistance. The electrical resistance, R, can be represented by the following equation:

$$R = \frac{\rho l}{wt} \qquad \text{EQ. 1}$$

where p is the resistivity of the material, w is the width of the conductor, t is the thickness of the conductor, and l is the length of the conductor.

The leads (i.e., traces) typically are fabricated to minimize their electrical resistance. Therefore, the length and resistivity of the leads desirably are minimized, while the thickness and width desirably are maximized. In one embodiment, the leads are composed of gold. Other suitable trace forming materials include platinum, copper, aluminum, and silver.

The properties of the reservoir cap are similarly defined. The electrical resistance of the cap can be controlled by its geometry, while its physical properties should increase the power efficiency of the device. Generally, an electrically resistive material should be selected so that the optimal amount of electrical power is converted into heat at the reservoir cap. A peak in efficiency occurs between the two relatively low-efficiency configurations of a very low-resistance reservoir cap and a very high-resistance reservoir cap. A very low-resistance reservoir cap produces small temperature increases per unit power because resistive heat generation is limited. In comparison, a very high-resistance reservoir cap reduces the amount of current flow through the device and therefore also produces small temperature increases per unit power. Between these two extremes lies a region of favorable efficiency. Other important physical properties are thermal diffusivity, thermal conductivity, and melting temperature. Reservoir caps having lower thermal diffusivities and conductivities will retain the heat in the reservoir cap, requiring less energy to be generated in the reservoir cap to rupture the cap. Additionally, reservoir caps composed of a material with a lower melting temperature that the material forming the leads will require less energy to rupture the cap. Additional parameters include physical properties such as the yield and failure strengths, and thermal expansion coefficients.

In some embodiments, the application of an electric current through the reservoir cap, via the input lead and output lead that are connected thereto, causes the temperature of the reservoir cap to be increased preferentially compared to the temperature of the leads.

Representative examples of suitable reservoir cap materials include gold, copper, aluminum, silver, platinum, titanium, palladium, various alloys (e.g., Au/Si, Au/Ge, Pt—Ir, Ni—Ti, Pt—Si, SS 304, SS 316), and silicon doped with an impurity to increase electrical conductivity, as known in the art. In one embodiment, the reservoir cap is in the form of a thin metal film. In another embodiment, the electrically conductive material of the reservoir cap is silicon that has been doped with boron.

In one embodiment, the reservoir cap is part of a multiple layer structure. In one embodiment, the reservoir cap is made of multiple metal layers, such as a multi-layer/laminate structure of platinum/titanium/platinum. For example, the top and bottom layers could be selected for adhesion layers on (typically only over a portion of) the reservoir cap to ensure that the reservoir cap adheres to/bonds with both the substrate area around the reservoir opening and a dielectric overlayer. In one specific example, the structure is titanium/platinum/titanium/platinum/titanium, where the top and bottom layers serve as adhesion layers, and the platinum layers provide extra stability and protection to the main, central titanium layer. The thickness of these layers could be, for example, about 300 nm for the central titanium layer, about 15 nm for each of the platinum layers, and between about 10 and 15 nm for the adhesion titanium layers.

The metallic leads can be connected to the reservoir cap using standard deposition techniques. In other embodiments, the leads and reservoir caps are fabricated in the same process step, of same material.

Design Configurations

There are several suitable approaches to making the temperature of the reservoir cap increase locally when an electrical current is applied.

Figure 1B:
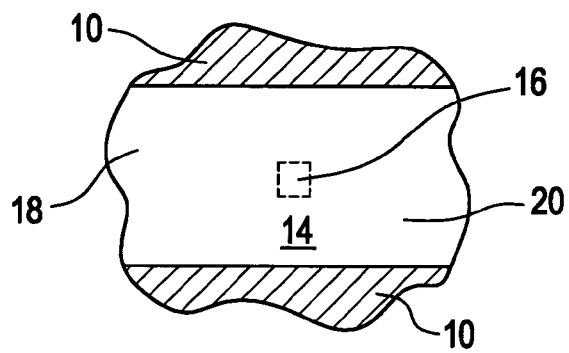

In one embodiment, the activation system includes conductive leads to each of the reservoir caps, wherein the leads and caps are formed of the same material (e.g., during the same processing step). An example of this embodiment is illustrated in FIGS. 1A and 1B, which, for simplicity, shows only one reservoir in a substrate portion. (Though not illustrated here, a substrate, or a device, could have two or more reservoirs.) Specifically, the device includes substrate 10 having reservoir 12, which is closed by reservoir cap 16. Conductive material 14 applied onto the surface of the substrate forms the reservoir cap 16, input lead 18, and output lead 20. To rupture the reservoir cap, the temperature of the reservoir cap increases locally by applying a current through conductive material when the reservoir cap is in contact with (e.g., the device is placed in) a medium that is less thermally conductive than the substrate. Although an equal amount of heat is generated in the leads and in the reservoir cap, the heat generated in the leads is dissipated into and through the substrate. If the medium in which the reservoir cap is suspended is less thermally conductive than the substrate, the temperature of the reservoir cap will preferentially increase compared to the leads (e.g., the substrate would serve as a heat sink under the leads).

Figure 2A:
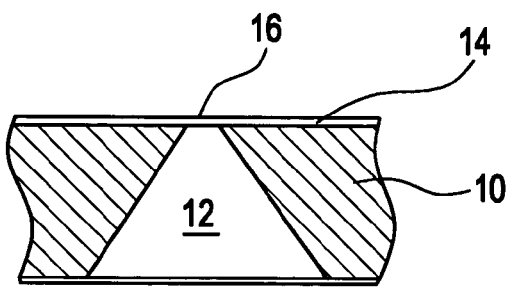
FIGS. 2A-B illustrate a cross-sectional view (FIG. 2A) and a plan view (FIG. 2B) of one embodiment of a portion of a device in which the reservoir cap and leads are formed of the same material and the width of the leads is greater than the width of the reservoir cap.
Figure 2B:
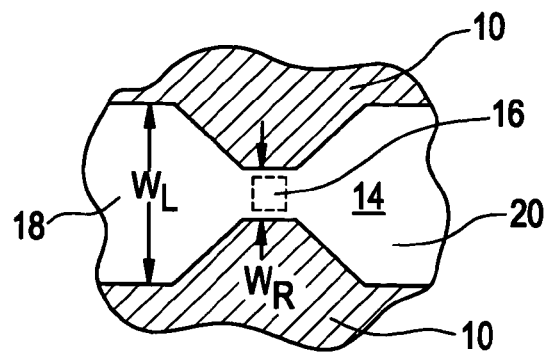
Figure 3A:
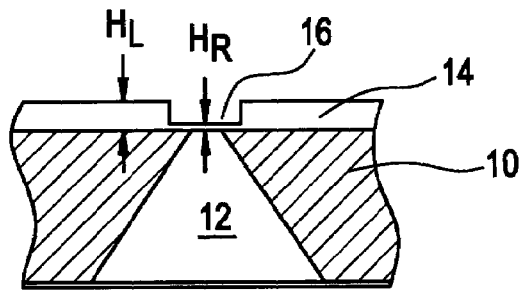
FIGS. 3A-B illustrate a cross-sectional view (FIG. 3A) and a plan view (FIG. 3B) of one embodiment of a portion of a device in which the reservoir cap and leads are formed of the same material and the thickness of the leads is greater than the thickness of the reservoir cap.
Figure 3B:
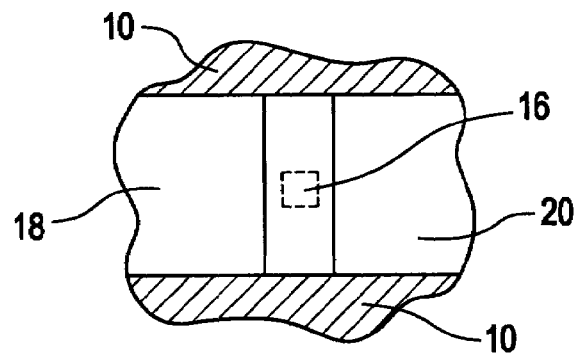

In another embodiment, the reservoir cap and leads have different widths or thicknesses to cause local heating of the reservoir cap. In one version, the reservoir cap and leads have identical thicknesses, and the reservoir cap has a smaller width than the leads. An example of this version is illustrated in FIGS. 2A and 2B, which shows substrate 10 having reservoir 12, which is closed by reservoir cap 16. Conductive material 14 applied onto the surface of the substrate forms the reservoir cap 16, input lead 18, and output lead 20, wherein the width of the portion of the conductive material forming the reservoir cap ($W_R$) is much less than the width of the portion of the conductive material forming the leads ($W_L$). Preferably, the ratio of the lead width:cap width is 2:1 or greater ($W_L:W_R \geq 2:1$). In another version, the reservoir cap has a smaller thickness than the leads. An example of this version is illustrated in FIGS. 3A and 3B, which shows substrate 10 having reservoir 12, which is closed by reservoir cap 16. Conductive material 14 applied onto the surface of the substrate forms the reservoir cap 16, input lead 18, and output lead 20, wherein the thickness of the portion of the conductive material forming the reservoir cap ($H_R$) is much less than the width of the portion of the conductive material forming the leads ($H_L$). Preferably, the ratio of the lead thickness:cap thickness is 2:1 or greater ($H_L:H_R \geq 2:1$). These "necking" designs cause localized heating of the reservoir cap upon application of an electrical current across the leads and through the reservoir cap, due to the increased current density resulting from the decrease in cross sectional area in the direction of current flow in the reservoir cap with respect to the leads.

Figure 4A:
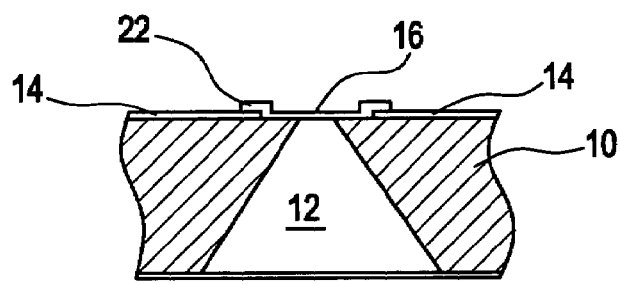
FIGS. 4A-B illustrate a cross-sectional view (FIG. 4A) and a plan view (FIG. 4B) of one embodiment of a portion of a device in which the reservoir cap and leads are formed of different materials.
Figure 4B:
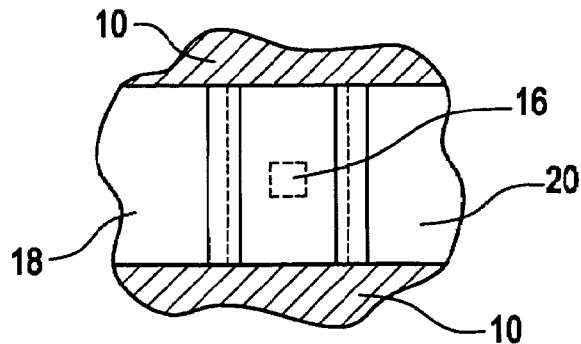

In yet another embodiment, the reservoir cap can be formed of a material that is different from the material forming the leads. The materials may be selected to take advantage of material properties that promote rupture of the reservoir cap with less power than would otherwise be required (e.g., for rupture by melting, a low $T_m$ may be desirable, or for rupture by thermal shock, a brittle material may be desirable). In one version, the reservoir cap is fabricated using a material with an electrical resistivity such that an optimal amount of electrical power is converted to heat in the reservoir cap. In another version, the reservoir cap can be formed of a material having a melting point which differs from (i.e., is higher or lower than) the melting point of the material forming the leads. For example, the leads could be formed of gold, which melts at approximately 1064° C., and the reservoir cap could be formed of the eutectic composition of gold and silicon, which melts at approximately 363° C. In yet another version, the reservoir cap can be formed of a material have a lower thermal diffusivity or thermal conductivity than the leads, to retain heat in the reservoir cap. For example, the leads could be formed of gold, which has a thermal conductivity of approximately 300 W/m-K, and the reservoir cap could be formed of titanium, which has a thermal conductivity of approximately 20 W/m-K. Various combinations of these embodiments can be employed. An example of this embodiment is illustrated in FIGS. 4A and 4B, which shows substrate 10 having reservoir 12, which is closed by reservoir cap 16. Conductive material 14 and reservoir cap material 22 are applied onto the surface of the substrate to form the reservoir cap 16, input lead 18, and output lead 20. Input lead 18 and output lead 20 are electrically connected to reservoir cap material 22 which comprises reservoir cap 16.

Electrical efficiency can be improved by thermally isolating the reservoir cap from the substrate. By reducing the amount of heat loss to the substrate, the amount of electrical energy to thermally rupture the reservoir cap is reduced. One method of achieving thermal isolation is to fabricate the reservoir cap on a shelf of dielectric material. This shelf serves as a structural support for the reservoir cap while greatly reducing heat loss to the substrate. See FIGS. 6 and 7. Exemplary values for the total thickness of this dielectric material range from 0.1 µm to 10 µm. The dielectric material would then be removed from directly underneath the reservoir cap before operation of the device. Examples of suitable dielectric materials include silicon dioxide, silicon nitride, and silicon carbide.

Figure 6:
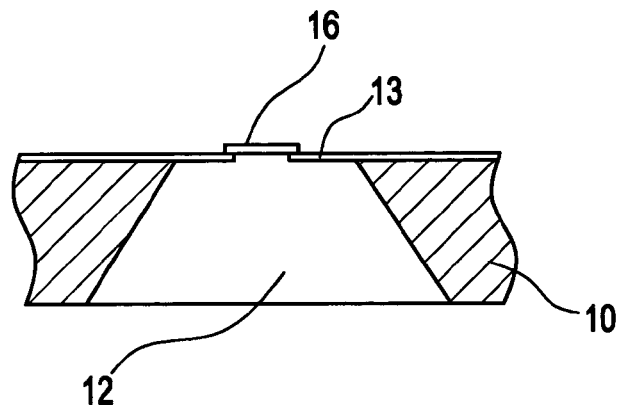
FIG. 6 is a cross-sectional view of one embodiment of a portion of a device wherein the reservoir cap is thermally isolated from the substrate by a dielectric material.
Figure 7A:
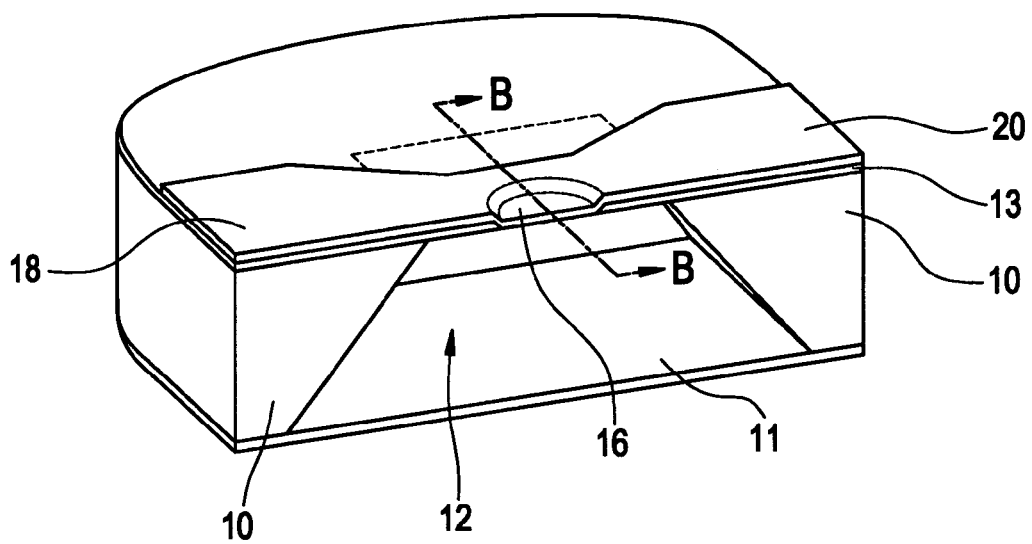
FIG. 7A is a perspective/cross-sectional view (FIG. 7A) of another embodiment of a portion of a device with a reservoir cap thermally isolated by a dielectric material.
Figure 7B:
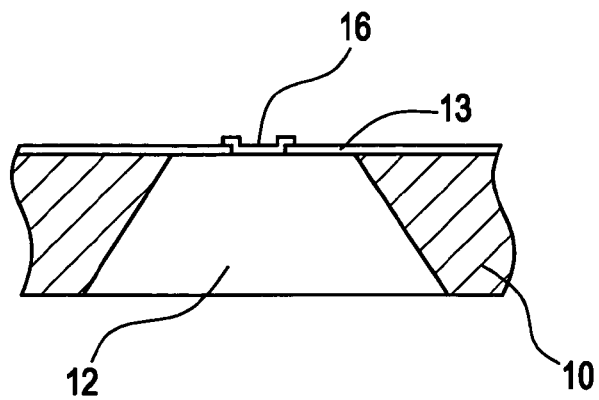
FIG. 7B is a cross-sectional view, taken along line B-B in FIG. 7A, illustrating the same embodiment.

In one embodiment, a dielectric material such as silicon nitride or silicon dioxide is deposited on the substrate. Reservoirs are formed in the substrate by a method, such as wet anisotropic etching. The reservoir cap and leads are then formed by deposition and selective etching. The dielectric material is then removed directly underneath the reservoir cap by a selective method, such as laser-induced chemical etching, yielding a configuration such as shown in FIG. 6, which shows device reservoir 12 covered by reservoir cap 16, which is thermally and electrically isolated from substrate 10 by dielectric material layer 13. In another embodiment, a dielectric material such as silicon nitride is deposited on a silicon substrate. This material is then selectively removed at the future location of the reservoir cap. Silicon dioxide (a "thermal oxide") is then thermally grown on the substrate. Because this step involves a chemical reaction with the silicon substrate, thermal oxide will only be present in the area where the silicon nitride has been removed. Reservoirs are then etched and the reservoir cap and leads are formed as described above. The thermal oxide is then removed from underneath the reservoir cap in an etching step that is selective against silicon nitride. An example of this type of etching step is immersion in buffered hydrofluoric acid. This process has an advantage over the process described above because it does not require the dielectric material to be removed from underneath each reservoir cap sequentially. That is, this process allows the dielectric material to be removed from every reservoir cap on the substrate in one etching step. In yet another embodiment, a dielectric material such as silicon nitride is deposited on a substrate. This material is then partially removed at the future location of the reservoir cap. Reservoirs are then etched and the reservoir cap and leads are formed as described above. The dielectric material is then thinned from the back of the substrate by a method such as timed reactive ion etching (RIE). This step is performed until the bottom of the reservoir cap is exposed, yielding a configuration such as shown in FIGS. 7A-B. These figures show a part of device, which includes a substrate 10 containing reservoir 12 (having bottom interior surface 11) wherein a reservoir cap 16 covers the reservoir and is integrally formed with input and output leads 18 and 20, and wherein dielectric material layer 13 is interposed between the conductive material that forms the reservoir cap/leads and the substrate.

It yet another embodiment, a layer of thermal oxide is grown on the silicon substrate before depositing silicon nitride. The reservoirs are then formed by etching from the back of the substrate by the method of deep reactive ion etching. This etching step is selective against silicon dioxide and will stop on the thermal oxide layer. The thermal oxide can then be removed by immersion in buffered hydrofluoric acid. In yet another embodiment, the reservoir cap is supported by a composite stack of a dielectric material along with a semiconductor or metal material to provide additional structural support. Exemplary values for the total thickness of this composite stack range from 0.1 µm to 100 µm. The top layer of this stack is desirably an electrical insulator to prevent electrical current flow between the reservoir cap and the supporting shelf.

Other Features

In further embodiments, a multi-layer structure is provided in which the leads and/or the reservoir caps are encapsulated or partially or completely covered on at least one side by another material. Examples include polymeric passivating layers (e.g., PTFE, parylene), as well as oxides, carbides, and nitride dielectrics, with either crystalline or amorphous structures.

In one embodiment, this other material is a dielectric material (e.g., silicon dioxide). The composition and dimensions of the dielectric layer(s) are selected so that the activation energy is sufficient to rupture both the reservoir cap and the dielectric layer(s). The dielectric material can thermally insulate the reservoir cap and leads from the environment, which can increase the efficiency of the conversion of electrical energy to thermal energy in the reservoir cap. In addition, the dielectric material can serve as a protective barrier, reducing or eliminating undesirable contact or reactions (e.g., oxidation) between the reservoir cap and the environment and/or between the reservoir cap and the reservoir contents. In some embodiments, the dielectric material can passivate the reservoir cap material. In other embodiments, the dielectric material can increase the strength, biocompatibility, biostability, and/or hermeticity. In one embodiment, the dielectric material in contact with the reservoir cap is formed or patterned to create a structure that provides mechanical support to the reservoir cap.

Figure 5A:
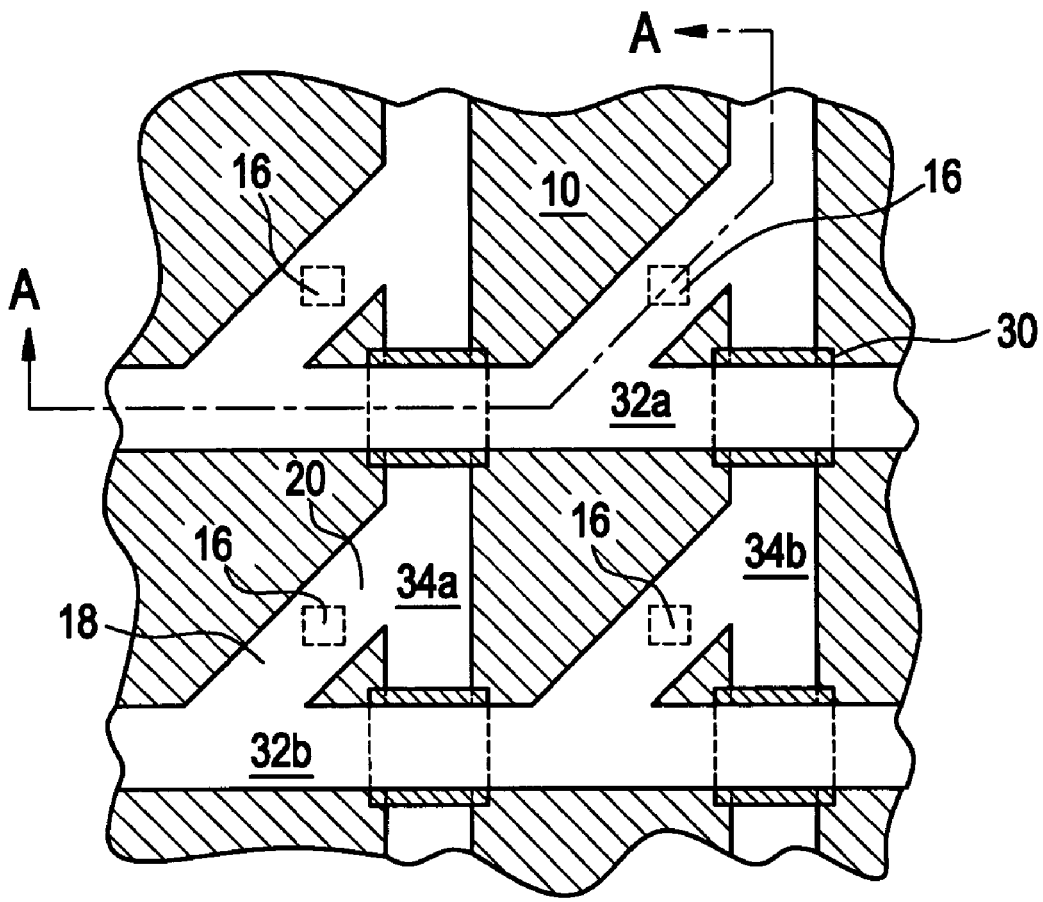
FIG. 5A is a plan view of one embodiment of a device with four reservoirs arranged in a square matrix with input leads connected in parallel by row and the output leads connected in parallel by column.
Figure 5B:
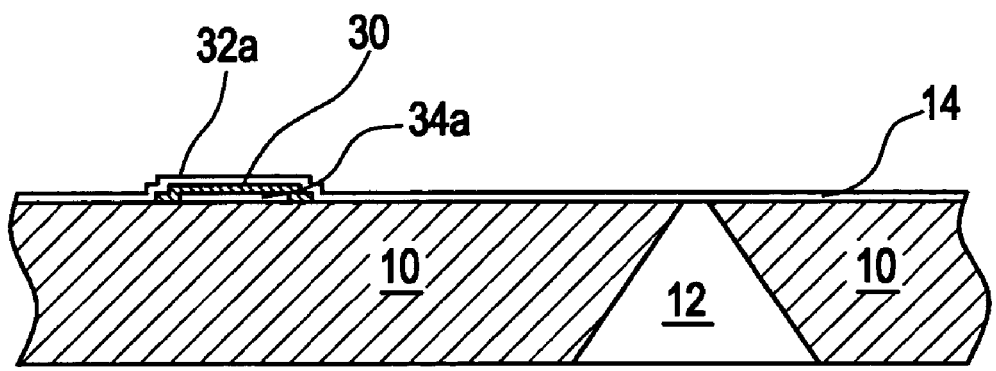
FIG. 5B is a cross-sectional view, taken along line A-A in FIG. 5A, illustrating how the conductor columns and leads are electrically insulated from one another where they overlap.

In one embodiment, the device comprises at least four or more reservoirs positioned in a two-dimensional array in the substrate. For instance, the reservoirs could be arrayed in the substrate on a square matrix, with the input side of the reservoir caps electrically connected in parallel by row, and the output side of the reservoir caps electrically connected in parallel by column. One example of this embodiment is illustrated in FIGS. 5A and 5B, which shows conductor material 14 forming rows 32a and 32b and columns 34a and 34b. The conductor material 14 also forms input leads 18, output leads 20, and reservoir caps 16. In an alternative design, which still uses the interconnected rows and columns, the reservoir caps are formed of a different material than the leads (or rows or columns of conductor material). An insulating material 30 is provided at the intersection of the columns and rows to prevent short-circuiting. As shown in FIG. 5B, the insulating material can be provided between the upper surface of the column and the lower surface of the row. This embodiment provides a matrix-addressed array with significantly reduced I/O requirements.

As illustrated in FIGS. 5A and 5B, the electrically conductive reservoir caps form electrical connections between the rows and columns of the array. When applying a voltage/current to a designated row and column to activate the reservoir cap at the intersection of the row and column, the connections cause current to flow through other reservoir caps. The magnitude of the current through any non-addressed cap (i.e., reservoirs not selected for opening at a particular time) will depend on its proximity to the reservoir cap being addressed (i.e., reservoirs selected for opening at the particular time), and factors such as the resistances of the reservoir caps and input/output leads (leads, rows and columns). For example, if an open circuit between the input and output lead is created when the reservoir cap ruptures, the current through the non-addressed reservoir caps will increase. Depending on the location of the addressed cap, the current through the non-addressed cap may increase sufficiently to cause it to rupture. This problem is most likely to occur when the addressed reservoir cap is the penultimate cap in a row or column, because the unintended current through the final cap in that row or column will be relatively large. The problem of unintended rupture can be prevented, for example, by modifying the design to include additional conducting paths. For example, an additional row and additional column could be added to the array, and conducting elements added at each of the intersections. These could be made of the same material as the reservoir caps, but would not be located over reservoirs. The purpose of these additional conductors would be to prevent an operable reservoir cap from being the final cap in any row or column and thus being exposed to relatively large unintended currents. In another approach, the inadvertent rupture of reservoir caps can be prevented by using caps which rupture, but do not create an open circuit (or retain essentially the same electrical resistance) between the input and output leads. This configuration, however, may prevent confirmation of reservoir opening by resistance measurement.

There may be applications where the passage of current through non-addressed reservoir caps in the array is undesirable. For example, drug molecules within the reservoir may be temperature sensitive and the heat generated could affect their stability. The addition of a rectifying element, such as a diode, in series connection with each reservoir cap, could be used to eliminate unintended currents. (Such a feature is shown, for example, in FIG. 6 of U.S. Pat. No. 4,089,734 and FIG. 1 of U.S. Pat. No. 6,403,403.) The diode could be a semiconductor junction diode, or a Schottky barrier diode. If a silicon substrate is used in the controlled release device, then the substrate and rectifying element could be integrally formed. The processes of introducing impurities into semiconductors to modify its conductivity and majority charge carrier, such as diffusion or ion implantation, and creating metal to semiconductor contacts, are well known. These could be integrated into the microchip fabrication process. Alternatively, specific activation of a reservoir cap can be accomplished by integrating a transistor with each reservoir cap, as described in U.S. Pat. No. 4,209,894 for a fusible-link memory array. In one embodiment, such a matrix approach is accomplished with transistors. Where transistors are integrated onto a microchip substrate, other active electronic components such as multiplexing switches optionally may also be able to be integrated into the microchip.

In one embodiment, transistor logic is used to construct a demultiplexer, in which a binary signal carried on several conductors is decoded and used to route an activation signal to a certain reservoir. In another embodiment, transistor logic is used to construct a shift register, in which a series of pulses on a single conductor is decoded and used to route an activation signal to a certain reservoir.

The integration of semiconductor components on the microchip greatly reduces the number of connections from the microchip to external electronics. For example, a microchip containing 400 reservoirs that are addressed individually requires 400 interconnects plus 1 common connection for returning current. By using a matrix addressing approach, the number of interconnects is reduced to 40, consisting of 20 row connections and 20 column connections. By using an integrated demultiplexer, the number of interconnects is reduced to 12, consisting of a 9 addressing inputs (a 9-digit binary number can be used to address over 400 reservoirs), an activation signal input, and power and ground connections. With an integrated shift register, only a serial input, a clock signal, and power and ground connections are required. In this example, semiconductor integration reduces the required number of interconnects by two orders of magnitude.

Electric Power Source and Activation Means

The device for controlled release or exposure includes a source of electric power for applying an electric current through the electrical input lead, the electrical output lead, and the reservoir cap connected therebetween in an amount effective to rupture the reservoir cap. Power can be supplied to the reservoir opening system locally by a battery or (bio) fuel cell or remotely by wireless transmission, as described for example in U.S. Patent Application Publication No. 2002/0072784. Criteria for selection of a power source include small size, sufficient power capacity, the ability to be integrated with the activation means, the ability to be recharged, and the length of time before recharging is necessary. Batteries can be separately manufactured or can be integrated with the delivery device.

The hardware, electrical components, and software needed to control and deliver the electric current from this power source may be referred to herein as "activation means." The activation means facilitates and controls reservoir opening. The activation means typically includes a microprocessor. In one embodiment, the operation of the reservoir opening system will be controlled by an on-board (e.g., within an implantable device) microprocessor. In another embodiment, a simple state machine is used, as it typically is simpler, smaller, and/or uses less power than a microprocessor.

For example, in one embodiment, a microchip drug delivery device includes a substrate having a two-dimensional array of reservoirs arranged therein, a release system comprising drug molecules contained in the reservoirs, reservoir caps comprising or consisting of an electrically conductive material covering each of the reservoirs, a pair of conductive leads (i.e., an input lead and an output lead) electrically connected to each reservoir cap, a source of electric power (e.g., a battery or capacitor), and activation means for selectively directing an electrical current from the power source through the reservoir cap, via the leads. The power source provides the current effective to rupture the reservoir cap, thus opening the selected reservoir(s) to release the drug molecules for delivery, e.g., to an implant site.

The activation means generally includes an input source, a microprocessor, a timer, a demultiplexer (or multiplexer). In one embodiment, the timer and (de)multiplexer circuitry can be designed and incorporated directly onto the surface of the substrate during fabrication.

The microprocessor directs power to a specific reservoir cap, as directed, for example, by an EPROM (erasable programmable read only memory), remote control, or biosensor. In various embodiments, the microprocessor is programmed to initiate rupture of the reservoir cap at a pre-selected time or in response to one or more of signals or measured parameters. For example, a programmed sequence of events including the time a reservoir is to be opened and the location or address of the reservoir is stored into an EPROM by the user. When the time for exposure or release has been reached as indicated by the timer, the microprocessor sends a signal corresponding to the address (location) of a particular reservoir to the demultiplexer. The demultiplexer routes an input, i.e., an electric current, to the reservoir addressed by the microprocessor. In other examples, rupture of the reservoir cap is in response to receipt of a signal from another device (for example by remote control or wireless methods) or detection of a particular condition using a sensor such as a biosensor.

The criteria for selection of a microprocessor are small size, low power requirement, and the ability to translate the output from memory sources, signal receivers, or biosensors into an address for the direction of power through the demultiplexer to a specific reservoir on the delivery device. Selection of a source of input to the microprocessor such as memory sources, signal receivers, or biosensors depends on the microchip device's particular application and whether device operation is preprogrammed, controlled by remote means, or controlled by feedback from its environment (i.e., biofeedback).

Optionally, the activation means may provide an output signal. The output signal from the device, after conditioning by suitable circuitry if needed, will be acquired by the microprocessor. After analysis and processing, the output signal can be stored in a writeable memory chip, and/or can be sent (e.g., wirelessly) to a remote location away from the microchip device or other controlled delivery device.

In an optional embodiment, the electric current to a reservoir cap can be designed to shut off immediately following reservoir cap rupture if needed to prevent bubble formation at the reservoir opening that could otherwise occur in some cases if current path remains (i.e., if not a complete open circuit) after reservoir cap rupture and current continues to pass through the remnants of the reservoir cap. In alternative embodiments, it may be desirable for a partial circuit to remain (e.g., around the periphery of the reservoir opening) following reservoir cap rupture.

In one embodiment, the reservoir device/opening system comprises an electrical component or system for detecting an open electrical circuit between the leads of a reservoir cap that has been ruptured, to verify reservoir opening.

The manufacture, size, and location of the power source, microprocessor, EPROM, timer, (de)multiplexer, and other components are dependent upon the requirements of a particular application. In one embodiment, the memory, timer, microprocessor, and (de)multiplexer circuitry is integrated directly onto the surface of the microchip. The battery is attached to the other side of the microchip and is connected to the device circuitry by vias or thin wires. However, in some cases, it is possible to use separate, prefabricated, component chips for memory, timing, processing, and demultiplexing. In one embodiment, these components are attached to the backside of the microchip device with the battery. In another embodiment, the component chips and battery are placed on the front of or next to the microchip device, for example similar to how it is done in multi-chip modules (MCMs) and hybrid circuit packages. The size and type of prefabricated chips used depends on the overall dimensions of the microchip device and the number of reservoirs, and the complexity of the control required for the application.

Illustrative Embodiments

The myriad embodiments of devices that can be created to use the reservoir opening systems and methods described herein can be understood with reference to the following non-limiting illustrations and descriptions.

FIG. 8 illustrates a portion of one embodiment of a device which utilizes the electrothermal ablation release system described herein. The device 50 includes a substrate 52 which has four reservoirs, only two of which are shown (in cross-section): 54a and 54b. Reservoir caps 58a, 58b, 58c, and 58d cover the reservoirs to isolate the reservoir contents 56 that is stored/isolated within each reservoir. Sealing layer 80 encloses the reservoir distal the reservoir caps. (It is noted that a separate sealing layer is not required where the bottom surface of the reservoir is integrally formed with the sidewalls, e.g., where the reservoirs are formed into, but not extending through the substrate, and reservoir filling occurs prior to application of the reservoir cap over the reservoir.) Each reservoir cap is integrally formed in electrical connection with a pair of leads: Reservoir cap 58a is connected to input lead (this one not shown) and output lead 62a, reservoir cap 58b is connected to input lead 60b and to output lead 62b, reservoir cap 58c is connected to input lead 60c and output lead 62c, and reservoir cap 58d is connected to input lead 60d and to output lead 62d. The leads are connected to source of electric power 70 for applying an electrical current through each of the reservoir caps. Surface 72 is an insulator.

In one embodiment, the reservoir opening devices/methods described herein are incorporated into an implantable medical device for subcutaneous drug delivery, to release drugs into the subcutaneous region which then diffuse into regional tissue or into body fluid-containing structures, including, for example, the cardiovascular system, the lymphatic system, the respiratory system, the digestive system, the central nervous system (cerebral spinal fluid), the genitourinary system, or the eyes. With the device, a drug can be administered to treat one or more of these tissues or structures or fluids within the structures, or can be transported through these tissues or structures to distal treatment locations or to cellular binding sites.

In another embodiment, the reservoir opening devices/methods described herein are incorporated into an implantable medical device that provides direct communication between the source of the drug (e.g., a reservoir) and the particular fluid-containing structure of interest, so that when drug is released, it enters the fluid without contacting the subcutaneous region. This could be useful, for example, for administrating a drug that if released in the subcutaneous space would cause inflammation, irritation, other tissue injury/dysfunction, or would diffuse too slowly into a fluid-containing structure to achieve an effective concentration in the fluid (e.g., because of clearance mechanisms). For example, the device could directly release a therapeutic agent into one or more body cavities or tissue lumens, including an intrathecal space, an intracranial space, an abdominal/peritoneal space (e.g., for cancer therapy, endometriosis therapy), a thoracic space (e.g., for regional administration of drug in the treatment of lung cancer), an intrapericardial space (e.g., to treat mycarditis, arrythmia), a renal space, or a hepatic space. For example, the substrate could have a shape that is compatible with the fluid-containing structure, such as tubular to reside within a blood vessel, rounded and buoyant to float in the bladder, or curved to conform to the eye. The control circuitry and power needed to activate the reservoir caps can be located in a control module outside or inside of the fluid-containing structure. If the control module is located external to the fluid-containing structure, electrical conductors can be used to connect to the reservoir caps.

Figure 10:
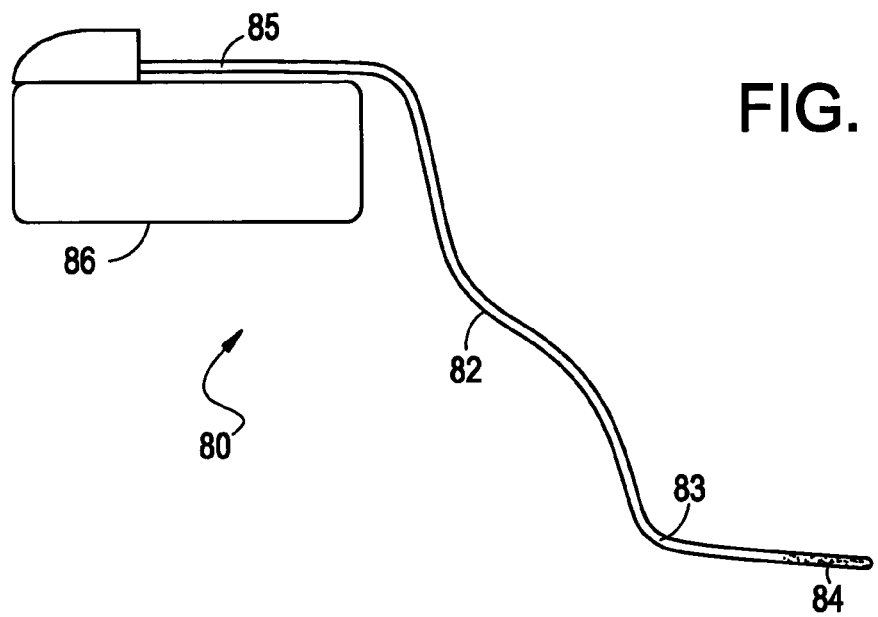
FIG. 10 is a perspective view of one embodiment of an implantable medical device that includes a catheter having drug-containing reservoirs at the distal end portion.
Figure 11A:
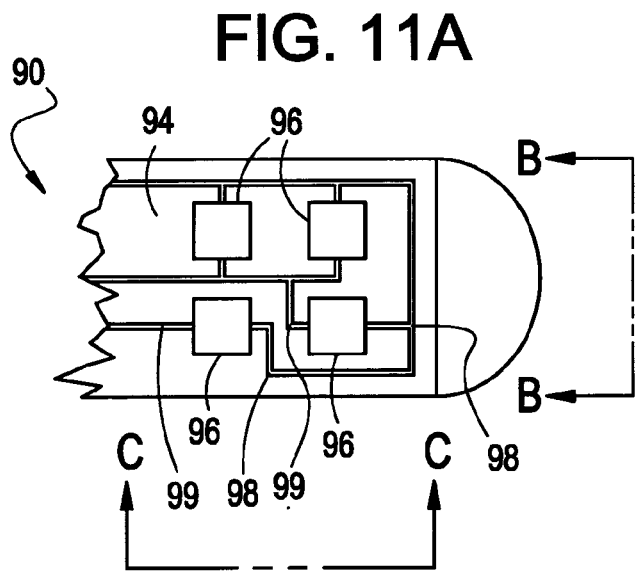
FIG. 11A is a plan view of one embodiment of the distal end portion of a catheter having an array of drug-containing reservoirs covered by reservoir caps that can be activated/opened using electrothermal ablation as described herein.
Figure 11B:
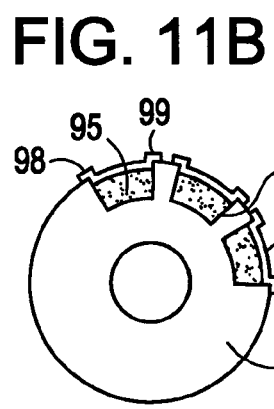
FIG. 11B is a cross-sectional view of the device shown in FIG. 11A, taken along line B/B.
Figure 11C:
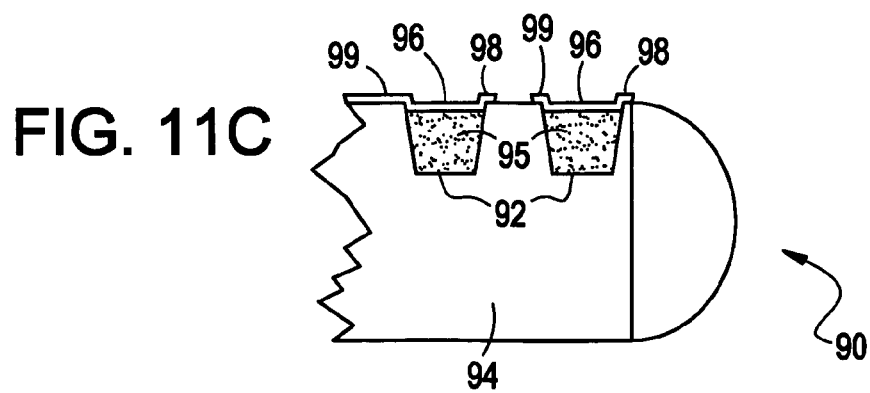
FIG. 11C is a cross-section view of the device, taken along line C/C.

FIG. 10 illustrates one embodiment of a medical device 80 which includes a catheter 82 which can be inserted into the tissue lumen or structure of interest and which has one or more drug-containing reservoirs 84 fabricated therein, for example at a distal portion 83 of the catheter. The body of the catheter serves as the substrate in which the reservoirs are fabricated, for example using soft lithography or other techniques known in the art. For example, tens or hundreds of micro-reservoirs could be arrayed around the catheter body at the distal tip portion. The reservoirs are hermetically sealed by conductive reservoir caps, which are electrically connected to a power source and can be disintegrated by electrothermal ablation as described herein. Advantageously, the power source and control hardware 86 can be located at a proximal end of the catheter 85, so they need not fit into or be located at the delivery site. The electrical traces could be build into the catheter body or supported on an inner or outer surface of the catheter body. See U.S. Patent Application No. 2002/0111601, which disclosed one embodiment of a catheter type implantable medical device, but which utilizes a different reservoir opening technology than the electrothermal ablation system described herein. FIGS. 11A-C illustrates a catheter tip portion 90 which has reservoirs 92 is substrate/catheter body 94, wherein the reservoirs contain therapeutic agent 95 and are covered by conductive reservoir caps 96, each of which are connected to input and output electrical leads 98 and 99, respectively.

Optionally, the catheter can have an internal fluid passageway extending between a proximal end portion and a distal end portion. The fluid passageway can be in communication with an infusion pump and a reservoir (e.g., a refillable reservoir containing a therapeutic fluid), so that the device can deliver a therapeutic fluid through the passageway to the delivery site. In one embodiment, the pump is placed abdominally in a subcutaneous pocket, and the catheter is inserted into the intrathecal space of the spine, tunneled under the skin and connected to the pump. Such an embodiment could be used, for example, in the management of chronic pain or for spasticity therapy. The microarray of drug-containing reservoirs can be provided (i) on or in the body of the catheter, (ii) in a substrate device that is located at the proximal end of the catheter and releases drug into an infusion fluid pumped across the microarray openings to form a fluid/drug mixture that is pumped through the fluid passageway of the catheter, or (iii) in a combination of these.

In one embodiment, the distal tip portion of the catheter includes one or more biological sensors to detect patient conditions that indicate the desirability or need for drug release. The sensors could extend from or be on the surface of the tip portion of the catheter body or could be located within one or more reservoirs. In one version, the device could include one catheter having a sensor on the distal end portion for implantation at a first site in vivo, and a second catheter having drug-containing reservoirs on the distal end portion for implantation at a second site in vivo. The proximal ends of the catheters would be connected with control hardware at a third site in vivo. For example, an EKG signal could be transmitted to the control module where it could be analyzed to recognize the onset of coronary ischemia. Such information could be used to justify the release of a thrombolytic agent into the venous circulation from a drug delivery system in direct communication with the venous circulation. Thrombolytic agents are currently delivered by intravenous injection because they cannot be released into the subcutaneous region. In another example, the sensor monitors the pulse in the legs or arms of the patient. Such a sensor could be used to justify the release of a vasodilator into a region, typically through an artery, to improve circulation when the pulse was attenuated. This design would be of value in treating patients with peripheral vascular disease, as these patients are not currently treated with vasodilators because no practical delivery systems are available.

In yet another embodiment, the drug-containing reservoirs are located external to the fluid-containing tissue structure. This configuration would include (i) one or more channels providing fluid communication between the reservoirs (when open) and the tissue structure, and (ii) reservoir caps to prevent body fluids from contacting the drug prior to activation. The channel may be filled with a different fluid, which is compatible with the drug, so that when the reservoir cap is activated, this fluid can facilitate release of the drug into the fluid-containing structure.

Figure 9A:
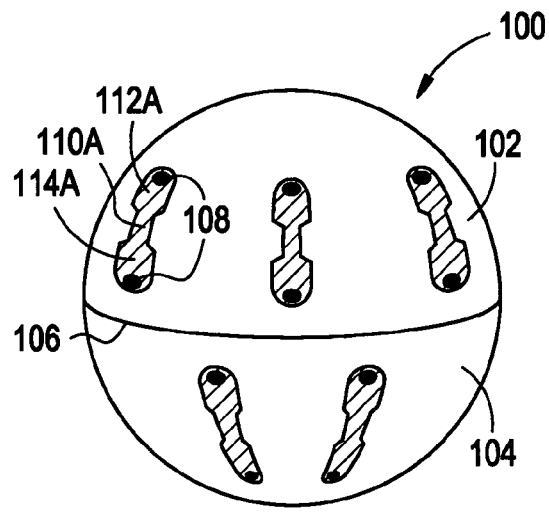
FIG. 9A is a perspective view of one embodiment of an implantable medical device having a spherical shape and an array of drug-containing reservoirs covered by reservoir caps that can be activated/opened using electrothermal ablation as described herein.
Figure 9B:
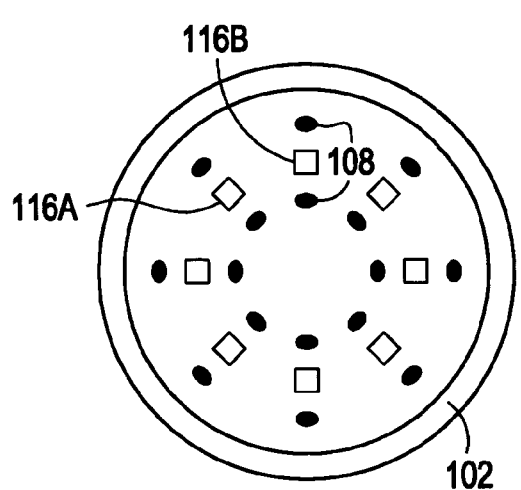
FIG. 9B is a plan view of the interior of the top case of the device.
Figure 9C:
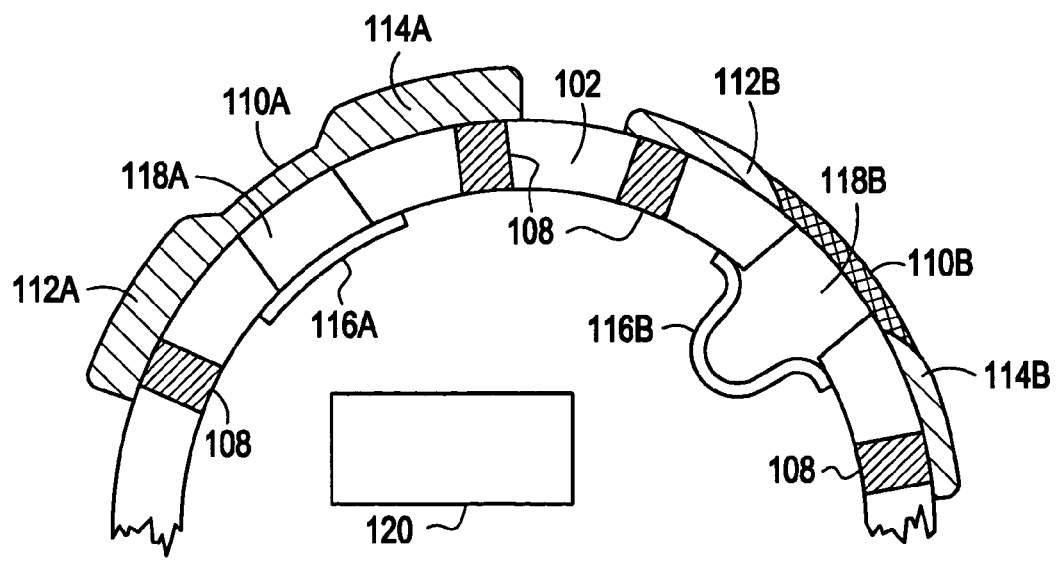
FIG. 9C is a cross-sectional view of a portion of the top case.

FIGS. 9A-C illustrate one embodiment of a spherical-shaped implantable device. Device 100 includes upper case portion 102 and lower case portion 104. These hemi-spherical portions are joined together at seal 106, forming a spherical encasement. The case portions 102, 106 serve as substrates in which reservoirs 118 are formed. The case portion could be made of titanium or (if hermeticity is not required) a polymer. Electrode pairs 108 penetrate through the encasement, operably connecting the input leads 112, the output leads 114, and reservoir caps 110, which are located on the outer surface of the encasement, with the control electronics and power systems, collectively 120, which are located inside the encasement. The reservoir can reside only in the substrate, as shown by reservoir 118A and reservoir seal 116, or the reservoir can include a supplementation portion that extends into the encasement beyond the substrate, as shown by reservoir 118B and reservoir seal/extension portion 116B. In an alternative embodiment, which is not shown, the reservoir does not extend all the way through the substrate (e.g., for embodiments where reservoir filling and sealing are conducted from the same side, exterior the encasement). Merely to illustrate the possible variations, leads 112A and 114A and reservoir cap 110A are formed of the same material, whereas leads 112B and 114B are formed of a different material than that of reservoir cap 110B.

Fabrication Methods

The basic methods of microfabricating and assembling certain of the components for a device, such as the substrate, reservoirs, and reservoir contents, is as known in the art, particularly those methods described in U.S. Pat. No. 5,797, 898; U.S. Pat. No. 6,123,861; U.S. Patent Application Publication No. 2002/0107470; and U.S. Patent Application Publication No. 2002/0151776, which are hereby incorporated by reference in their entirety. These basic device components are adapted to include the electrical leads and electrically resistive reservoir cap and the electrically induced thermal activation means described herein.

In one embodiment, soft lithography, microcontact printing, or the like is used. For example, these techniques can be useful for forming leads and reservoir caps on non-planar substrates. See, e.g., U.S. Pat. No. 6,180,239; No. 5,951,881; No, 6,355,198; and No. 6,518,168.

Fabrication of Electrically Resistive Reservoir Caps and Electrical Leads

In one embodiment, the reservoir caps and the leads are fabricated simultaneously from the same material, that is, they are integrally formed. For example, the reservoir caps and leads can be formed using photolithography and thin film deposition techniques known in the art. Alternatively, the leads and reservoir caps can be prefabricated and then surface mounted across the reservoir opening.

In other embodiments, the reservoir caps are formed in a separate step from formation and attachment of the leads. For example, the reservoir caps could be formed onto the substrate using photolithography and thin film deposition techniques, and then, either before or after reservoir filling, the leads could be added to the substrate in electrical contact with the reservoirs. The leads could also be formed before or after reservoir cap formation, where both would be formed before device filling. This later approach may be useful to enhance drug protection, for example.

In one example, reservoir caps are formed as follows: Photoresist is patterned in the form of reservoir caps on the surface of the substrate having the reservoirs covered by the thin membrane of insulating or dielectric material. The photoresist is developed such that the area directly over the covered opening of the reservoir is left uncovered by photoresist and is in the shape of a reservoir cap. A thin film of material is deposited on the substrate by methods such as evaporation, sputtering, chemical vapor deposition, solvent casting, slip casting, contact printing, spin coating, or other thin film deposition techniques known in the art. After film deposition, the photoresist is stripped from the substrate. This removes the deposited film, except in those areas not covered by photoresist (lift-off technique). This leaves material on the surface of the substrate in the form of reservoir caps. An alternative method involves depositing the material over the entire surface of the device, patterning photoresist on top of the thin film using ultraviolet (UV) or infrared (IR) photolithography, so that the photoresist lies over the reservoirs in the shape of reservoir caps, and etching the unmasked material using plasma, ion beam, or chemical etching techniques. The photoresist is then stripped, leaving thin film caps covering the reservoirs. Typical film thicknesses of the reservoir cap material is between 0.05 μm and several microns.

In the case where the reservoir cap is the same material as the leads, the lead-reservoir cap layer is continuous and there are no connections or interfaces. In the case where the reservoir cap and the lead are of dissimilar compositions, the interface/connection is an intermetallic junction. The connections to the power source can be made by traditional IC means, flip-chip, wirebonding, soldering, and the like.

An adhesion layer may be necessary to ensure adhesion between the substrate and the reservoir cap and leads. Some examples of adhesion layers are titanium, chromium, and aluminum. Techniques for employing adhesion layers are well known in the art.

Dielectric Coating

In some embodiments, insulating or dielectric materials are deposited over the reservoir cap, leads, or entire surface of the device by methods such as chemical vapor deposition (CVD), electron or ion beam evaporation, sputtering, or spin coating to protect the device or enhance biostability/biocompatibility. Examples of such materials include oxides, nitrides, carbides, diamond or diamond-like materials, or fluorocarbon films. (Some suitable materials are described in U.S. Patent Application Publication No. 2003/0080085, e.g., nanocrystalline diamond.) In one embodiment, the outer layer comprises a single layer or a multi-layer/laminate structure that includes combinations of silicon oxide ($SiO_x$), silicon nitride ($SiN_x$) or silicon carbide ($SiC_x$). In one embodiment, photoresist is patterned on top of the dielectric to protect it from etching except on the reservoir caps covering each reservoir. The dielectric material can be etched by physical or chemical etching techniques. The purpose of this film is to protect the reservoir caps and leads from corrosion, degradation, or dissolution in all areas where they do not have to be exposed to the surrounding environment, to shield electrically active components from the in vivo environment, and to enhance the biostability of the device materials.

In some embodiments, insulating materials such as silicon nitride ($SiN_x$) or silicon oxide ($SiO_x$) are deposited between the substrate and the leads by methods such as CVD, electron or ion beam evaporation, sputtering, or spin coating. The purpose of this film is to prevent electrical contact between any electrically active leads and the substrate, if the substrate is an electrical conductor. Such electrically conducting insulating layers are also deposed between layers of metal traces when they must be stacked on top of each other, for example as in devices that utilize matrix addressing of the reservoir caps.

Packaging

A device incorporating the electrothermal ablation opening technology described herein can be packaged or sealed as needed for particular applications (e.g., for implantation into patients). In one embodiment, the device is hermetically sealed by welding the substrate to one or more surfaces of a packaging structure. The term "packaging structure" refers to an enclosure, casing, or other containment device for encasing the substrate, control electronics, and power elements (e.g., battery or devices for receiving wireless transmission of power), so as to expose only the release side of the substrate or reservoir caps.

Using the Electrothermal Ablation Reservoir Opening Systems/Devices

The controlled release/exposure devices and systems described herein can be used in a wide variety of applications. Preferred applications include the controlled delivery of a drug, biosensing, or a combination thereof. Embodiments for some of these applications are described in the illustrative embodiments above, and other embodiments are detailed below.

In one embodiment, a microchip device, which includes the electrothermal ablation reservoir opening device described herein, is provided for implantation into a patient, such as a human or other vertebrate animal, for controlled drug delivery, locally, regionally, or systemically. In one embodiment, the microchip device can be implanted in vivo using standard surgical or minimally-invasive implantation techniques. Such microchip devices are especially useful for drug therapies in which one needs to very precisely control the exact amount, rate, and/or time of delivery of the drug. Exemplary drug delivery applications include the delivery of potent molecules, including, hormones (e.g., PTH), steroids, cytokines, chemotherapeutics, vaccines, gene delivery vectors, anti-VEGF aptamers, and certain analgesic agents.

In other embodiments, the electrothermal ablation reservoir opening device described herein is incorporated into a variety of other types and designs of implantable medical devices, such as the catheters and electrodes described in U.S. Patent Application Publication No. 2002/0111601. In another example, it could be incorporated into another medical device, in which the present devices and systems release drug into a carrier fluid that then flows to a desired site of administration, as illustrated for example in U.S. Pat. No. 6,491,666.

The devices have numerous in vivo, in vitro, and commercial diagnostic applications. The devices are capable of delivering precisely metered quantities of molecules and thus are useful for in vitro applications, such as analytical chemistry, drug discovery, and medical diagnostics, as well as biological applications such as the delivery of factors to cell cultures. In still other non-medical applications, the devices are used to control release of fragrances, dyes, or other useful chemicals. Other methods of using the devices for controlled release of molecules, as well as for controlled exposure or release of secondary devices, are described in U.S. Pat. No. 5,797,898; No. 6,123,861; No. 6,527,762; No. 6,491,666; No. 6,551,838 and U.S. Patent Application Publications No. 2002/0072784; No. 2002/0107470; No. 2002/0151776; No. 2002/0099359; and No. 2003/0010808.

Publications cited herein are incorporated by reference. Modifications and variations of the methods and devices described herein will be obvious to those skilled in the art from the foregoing detailed description. Such modifications and variations are intended to come within the scope of the appended claims.

We claim:

1. A device for the controlled release or exposure of reservoir contents comprising:
    a substrate having at least one reservoir;
    a discrete reservoir cap in register with the at least one reservoir and formed of an electrically conductive material, which prevents the reservoir contents from passing out from the device and prevents exposure of the reservoir contents to molecules outside of the device;
    an electrical input lead connected to and directly contacting said reservoir cap; and
    an electrical output lead connected to and directly contacting said reservoir cap, such that upon application of an electrical current through the reservoir cap, via the input lead and output lead, the reservoir cap is ruptured to release or expose the reservoir contents and the substrate is not ruptured.

2. The device of claim 1, further comprising a source of electric power for applying the electrical current.

3. The device of claim 1, wherein the application of electrical current through the reservoir cap causes the temperature of the reservoir cap to increase preferentially compared to the temperature of the leads.

4. The device of claim 1, wherein the reservoir cap is formed of a material having a melting point which differs from the melting point of the material forming the leads.

5. The device of claim 1, wherein the reservoir cap and leads are formed of the same material, and the reservoir cap has a smaller cross-sectional area in the direction of electric current flow.

6. The device of claim 5, wherein the leads and the reservoir cap have the same thickness, and the ratio of the width of the leads to the width of the reservoir cap is 2:1 or more.

7. The device of claim 5, wherein the reservoir cap has a thickness that is less than the thickness of the leads.

8. The device of claim 7, wherein the ratio of the thickness of the leads to the thickness of the reservoir cap is 2:1 or more.

9. The device of claim 1, wherein the reservoir cap is formed of a material which is different from the material forming the leads.

10. The device of claim 9, wherein the reservoir cap is formed of a material having a different resistivity than the material forming the leads.

11. The device of claim 9, wherein the reservoir cap is formed of a material having a different thermal diffusivity or thermal conductivity than the material forming the leads.

12. The device of claim 1, wherein the reservoir cap comprises a metal film.

13. The device of claim 12, wherein the metal film comprises of a metal selected from the group consisting of gold, platinum, titanium, copper, aluminum, silver, gold/silicon alloys, gold/germanium alloys, platinum/iridium, nickel/titanium, and platinum silicide.

14. The device of claim 1, wherein the reservoir cap comprises multiple layers of metal or multiple layers of metal and semiconductor.

15. The device of claim 1, further comprising one or more layers of a dielectric material on at least a portion of the reservoir cap, the leads, or both.

16. The device of claim 15, wherein the dielectric material comprises oxides, nitrides, carbides, diamond, fluorocarbon films, or combinations thereof.

17. The device of claim 1, wherein the reservoir contents are located in two or more reservoirs provided in the substrate.

18. The device of claim 1, wherein the reservoir contents comprises at least one therapeutic or prophylactic agent.

19. The device of claim 18, wherein the therapeutic or prophylactic agent comprises a parathyroid hormone.

20. The device of claim 19, wherein the parathyroid hormone comprises a human parathyroid hormone.

21. The device of claim 18, wherein the reservoir contents comprises human parathyroid hormone hPTH(1-34).

22. The device of claim 1, which is a subcomponent of an implantable drug delivery device.

23. The device of claim 22, further comprising at least one sensor indicative of a physiological condition, at least one electrode for providing electrical stimulation to the body, a catheter, a pump, or a combination thereof.

24. The device of claim 1, which is part of a microchip device.

25. The device of claim 1, which is part of an implantable catheter.

26. The device of claim 1, wherein the reservoir contents comprises human parathyroid hormone hPTH(1-34).

27. A device for the controlled release or exposure of reservoir contents comprising:
    a substrate;
    a plurality of discrete reservoirs provided in the substrate;
    reservoir contents comprising molecules, a secondary device, or both, located in said plurality of reservoirs;
    a plurality of discrete reservoir caps, each reservoir cap covering each reservoir to isolate said reservoir contents within said reservoir, each reservoir cap comprising an electrically conductive material;
    a pair of conductive leads electrically connected to and directly contacting each of said reservoir caps, the pair comprising an electrical input lead and an electrical output lead; and
    a source of electric power for applying an electrical current through each reservoir cap, via said pair of conductive leads, in an amount effective to rupture each of the reservoir caps and not the substrate.

28. The device of claim 27, comprising four or more reservoirs positioned in a two-dimensional array in the substrate.

29. The device of claim 28, wherein the input leads to the reservoir caps are electrically connected in parallel by rows of the array and the output leads from the reservoir caps are electrically connected in parallel by columns of the array.

30. The device of claim 27, further comprising an electrical component or system for detecting an open electrical circuit between the leads of a reservoir cap that has been ruptured, to verify reservoir opening.

31. The device of claim 27, wherein the reservoir contents comprises a release system comprising drug molecules.

32. The device of claim 31, wherein the drug molecules comprise a parathyroid hormone.

33. The device of claim 32, wherein the parathyroid hormone comprises a human parathyroid hormone.

34. The device of claim 27, further comprising activation means for controlling said application of electric current through each reservoir cap.

35. The device of claim 34, wherein said activation means comprises a microprocessor or state machine.

36. The device of claim 34, wherein said activation means comprises an active electronic component effective to eliminate unintended reservoir opening.

37. The device of claim 36, wherein the active electronic component comprises a diode or transistor.

38. The device of claim 27, wherein the substrate is in a shape selected from the group consisting of disks, cylinders, or spheres.

39. The device of claim 27, wherein a dielectric material is interposed between the reservoir cap and the substrate to thennally isolate the reservoir cap from the substrate.

40. A device to provide the controlled release of a drug contained therein to a body of a human or animal comprising:
   a discrete reservoir cap formed of an electrically conductive material, which prevents the drug from passing out from the device to the body;
   a pair of conductive leads electrically connected to and directly contacting said reservoir cap, the pair comprising an electrical input lead and an electrical output lead; and
   activation means for selectively applying an electrical current through said reservoir cap, via the input lead and output lead, to locally heat the reservoir cap causing the reservoir cap to rupture to enable the drug to pass outward from the device to the body,
   wherein (i) the reservoir cap and the input and output leads are designed to provide upon the application of electrical current an increase in electrical current density in the reservoir cap relative to the current density in the input and output leads, (ii) the material forming the reservoir cap has a different electrical resistivity, thermal diffusivity, thermal conductivity, and/or a lower melting temperature than the material forming the input and output leads, or (iii) the reservoir cap and the input and output leads are designed to provide upon the application of electrical current an increase in electrical current density in the reservoir cap relative to the current density in the input and output leads, and the material forming the reservoir cap has a different electrical resistivity, thermal diffusivity, thermal conductivity, and/or a lower melting temperature than the material forming the input and output leads.

41. The device of claim 40, further comprising at least one reservoir for containing the drug, said reservoir being at least partially enclosed by the reservoir cap.

42. The device of claim 41, comprising a plurality of reservoirs and a plurality of reservoir caps.

43. The device of claim 40, wherein the drug comprises a parathyroid hormone.

44. The device of claim 40, wherein the parathyroid hormone comprises a human parathyroid hormone.

45. The device of claim 44, wherein the reservoir contents comprises human parathyroid hormone hPTH(1-34).

46. A medical device for the controlled exposure of a sensor comprising:
   a substrate;
   a plurality of reservoirs provided in the substrate;
   a plurality of sensors located in said plurality of reservoirs;
   a discrete reservoir cap covering each reservoir to isolate said sensor within said reservoir, each reservoir cap comprising an electrically conductive material;
   a pair of conductive leads electrically connected to and directly contacting said reservoir cap, the pair comprising an electrical input lead and an electrical output lead; and
   a source of electric power for applying an electrical current through each reservoir cap, via said pair of conductive leads, in an amount effective to rupture the reservoir cap and not the substrate.

47. The device of claim 46, wherein the sensors detect a physiological condition in a patient.

48. The device of claim 47, wherein the sensor is a biosensor.

49. The device of claim 48, wherein the biosensor measures the concentration of glucose, urea, calcium, or a hormone in the patient.

50. A device for the controlled release or exposure of reservoir contents comprising:
   a reservoir cap formed of an electrically conductive material, which prevents the reservoir contents from passing out from the device and prevents exposure of the reservoir contents to molecules outside of the device;
   an electrical input lead connected to and directly contacting said reservoir cap; and
   an electrical output lead connected to and directly contacting said reservoir cap, such that upon application of an electrical current through the reservoir cap, via the input lead and output lead, the reservoir cap is ruptured to release or expose the reservoir contents,
   wherein (i) the reservoir cap and the input and output leads are designed to provide upon the application of electrical current an increase in electrical current density in the reservoir cap relative to the current density in the input and output leads, (ii) the material forming the reservoir cap has a different electrical resistivity, thermal diffusivity, thermal conductivity, and/or a lower melting temperature than the material forming the input and output leads, or (iii) the reservoir cap and the input and output leads are designed to provide upon the application of electrical current an increase in electrical current density in the reservoir cap relative to the current density in the input and output leads, and the material forming the reservoir cap has a different electrical resistivity, thermal diffusivity, thermal conductivity, and/or a lower melting temperature than the material forming the input and output leads.

* * * * *